(12) United States Patent
Newcom et al.

(10) Patent No.: US 7,960,376 B2
(45) Date of Patent: Jun. 14, 2011

(54) BENZO-FUSED HETEROCYCLES

(75) Inventors: Jason S. Newcom, Northford, CT (US); Carla M. Gauss, White Plains, NY (US); Gary R. Gustafson, Ridgefield, CT (US)

(73) Assignee: Cara Therapeutics, Inc., Shelton, CT (US)

( * ) Notice: Subject to any disclaimer, the term of this patent is extended or adjusted under 35 U.S.C. 154(b) by 368 days.

(21) Appl. No.: 12/207,601

(22) Filed: Sep. 10, 2008

(65) Prior Publication Data

US 2009/0075973 A1 Mar. 19, 2009

Related U.S. Application Data

(60) Provisional application No. 60/993,872, filed on Sep. 14, 2007.

(51) Int. Cl.
*C07D 279/16* (2006.01)
*A61K 31/5415* (2006.01)

(52) U.S. Cl. ........ 514/227.8; 544/51; 544/52; 514/228.2

(58) Field of Classification Search .................... 544/51, 544/52; 514/227.8, 228.2
See application file for complete search history.

(56) References Cited

U.S. PATENT DOCUMENTS

| 4,080,323 A | 3/1978 | Walser et al. |
|---|---|---|
| 4,118,386 A | 10/1978 | Walser |
| 4,687,777 A | 8/1987 | Meguro et al. |
| 2003/0139394 A1 | 7/2003 | Lubisch et al. |
| 2007/0010670 A1 | 1/2007 | Hirata et al. |
| 2007/0191603 A1 * | 8/2007 | Ackermann et al. ............ 544/50 |

FOREIGN PATENT DOCUMENTS

| WO | WO9925717 A1 | 5/1999 |
|---|---|---|
| WO | WO 9925717 A1 * | 5/1999 |
| WO | WO0066124 A1 | 11/2000 |
| WO | 2004014389 A1 | 2/2004 |
| WO | WO2004/014389 A2 | 2/2004 |
| WO | WO2005092872 A1 | 10/2005 |
| WO | 2006015259 A2 | 2/2006 |
| WO | WO2006/015259 A2 | 2/2006 |
| WO | 2007024949 A2 | 3/2007 |
| WO | WO2007/024949 A2 | 3/2007 |
| WO | WO2007/050425 A2 | 3/2007 |
| WO | 2007050425 A2 | 5/2007 |
| WO | WO2007093507 A1 | 8/2007 |
| WO | WO2008118141 A2 | 10/2008 |
| WO | WO2009035997 A3 | 3/2009 |

OTHER PUBLICATIONS

Vippagunta et al, "Crystalline Solids" Advanced Drug Delivery Reviews, vol. 48, pp. 3-26 (2001).*
Abou-Gharbia, M. et al., *Synthesis and Structure-Acivity Relationship of Substituted Tetrahydro- and Hexahydro-1,2-benzisothiazol-3-one 1,1-Dioxides and Thiadiazinones: Potential Anxiolytic Agents*, J. Med. Chem. (1989) vol. 32:1024-1033. Amer.Chem Soc.

* cited by examiner

*Primary Examiner* — Kahsay T Habte
(74) *Attorney, Agent, or Firm* — Algis Anilionis

(57) ABSTRACT

The present invention provides benzo-fused heterocyclic compounds having the structure of formula I, as well as prodrugs, stereoisomers, racemates, salts, hydrates, solvates, acid salt hydrates and isomorphic crystalline forms thereof.

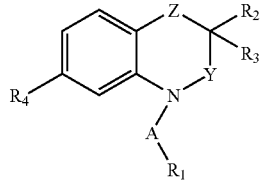

The compounds directly or indirectly modulate the activity of one or more cannabinoid receptors and can be incorporated into pharmaceutical preparations that are useful for the prevention and treatment of a variety of diseases and conditions, including pain, inflammation and pruritis.

12 Claims, No Drawings

BENZO-FUSED HETEROCYCLES

RELATED APPLICATION

This application claims the benefit of U.S. provisional patent application Ser. No. 60/993,872 filed Sep. 14, 2007, the specification of which is hereby incorporated by reference in its entirety.

BACKGROUND OF THE INVENTION

Classical cannabinoids such as the marijuana derived cannabinoid Δ9-tetra-hydrocannabinol, (Δ9-THC) produce their pharmacological effects through interaction with specific cannabinoid receptors in the body. So far, two cannabinoid receptors have been characterized: CB1, a receptor found in the mammalian brain and peripheral tissues and CB2, a receptor found only in the peripheral tissues. Compounds that are agonists or antagonists for one or both of these receptors have been shown to provide a variety of pharmacological effects. See, for example, Pertwee, R. G., Pharmacology of cannabinoid CB1 and CB2 receptors, Pharmacology and Therapeutics (1997) 74:129-180 and Di Marzo, V., Melck, D., Bisogno, T., DePetrocellis, L., Endocannabinoids: Endogenous Cannabinoid Receptor Ligands with Neuromodulator Action, Trends in Neuroscience (1998) 21:521-528. There is considerable interest in developing cannabinoids possessing high affinity for the CB2 receptor. Cannabinoid analogs that preferentially stimulate the CB2 receptor, directly or indirectly, have the potential to provide clinically useful effects without affecting the subject's central nervous system.

SUMMARY OF THE INVENTION

The present invention provides compounds having the structure of the shown below (formula I):

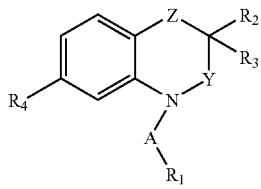

I

In formula I the linking group, A is CO, CONH, or $SO_2$; Y is $(CH_2)_p$; and Z is S, SO, $SO_2$ or O. The radical, $R_1$ is chosen from (i) $C_1$-$C_6$ alkyl; (ii) aryl optionally substituted with from 1 to 3 substituents independently chosen from halogen, $C_1$-$C_6$ alkyl, $CF_3$, $OCF_3$, $OR_{10}$, $COR_{10}$, $COOR_{10}$, $NR_{10}R_{11}$, $CONR_{10}R_{11}$; (iii) $C_3$-$C_8$ cycloalkyl; or (iv) 4- to 10-membered heterocyclyl, optionally substituted with from 1 to 3 substituents independently chosen from halogen, $C_1$-$C_6$ alkyl, $C_1$-$C_6$ alkoxy, $CF_3$, $OCF_3$, $OR_{10}$, $COOR_{10}$, $NR_{10}R_{11}$, $COR_{10}$, and $CONR_{10}R_{11}$. $R_2$ and $R_3$ are each independently H or $C_1$-$C_3$ alkyl. The radical, $R_4$ is (i) $COOR_5$; (ii) $CONR_5R_6$; (iii) aryl optionally substituted with from 1 to 3 substituents independently chosen from halogen, $C_1$-$C_6$ alkyl, $C_1$-$C_6$ alkoxy, $CF_3$ and $OCF_3$; or (iv) 5- to 10-membered heterocyclyl optionally substituted with from 1 to 3 substituents independently chosen from halogen, $CF_3$, $OCF_3$ and $R_{12}$. Radicals, $R_5$ and $R_6$ are each independently chosen from, H, $C_1$-$C_6$ alkyl, $C_1$-$C_6$ alkoxyalkyl, $(CH_2)_n$-aryl, $(CH_2)_n$—$C_3$-$C_{10}$ cycloalkyl and $(CH_2)_n$ (3- to 8-membered heterocyclyl); or $R_5$ is H, or $C_1$-$C_6$ alkyl and $R_6$ is chosen from $CR_7R_8R_9$ and —$NHCOR_{12}$. Alternatively, $R_5$ and $R_6$ taken together with the nitrogen atom to which they are bonded form a 4- to 10-membered heterocyclyl optionally substituted with from 1 to 3 substituents independently chosen from halogen, $C_1$-$C_6$ alkyl, $C_1$-$C_6$ alkoxy, $CF_3$, $OCF_3$, $OR_{10}$, $COOR_{10}$, $NR_{10}R_{11}$, $COR_{10}$, and $CONR_{10}R_{11}$. The radicals, $R_7$ and $R_8$ are each independently chosen from H and $C_1$-$C_6$ alkyl. Alternatively, $R_7$ and $R_8$ taken together with the carbon atom to which they are bonded form a 3- to 6-membered carbocyclyl group or a 3- to 6-membered heterocycyl. The radical, $R_9$ is chosen from $(CH_2)_p$—$OR_{13}$, $(CH_2)_p$—$NR_{13}R_{14}$, $(CH_2)_n COOR_{13}$, and $(CH_2)_n CONR_{13}R_{14}$; $R_{10}$ is (i) independently chosen from H, $C_1$-$C_6$ alkyl and $(CH_2)_n$—$C_3$-$C_8$ cycloalkyl; or (ii) aryl or heteroaryl, wherein each aryl or heteroaryl is optionally substituted with from 1 to 3 substituents independently chosen from, halogen, $CF_3$, $OCF_3$, $C_1$-$C_6$ alkyl, $C_1$-$C_6$ alkoxy. The radical, $R_{11}$ is independently chosen from H, $C_1$-$C_6$alkyl and CO—($C_1$-$C_6$alkyl).

Alternatively, $R_{10}$ and $R_{11}$ when taken together with the nitrogen to which they are bonded form a 5-6 membered heterocyclyl. Radical, $R_{12}$ is (i) chosen from $C_1$-$C_6$ alkyl, $C_1$-$C_6$ alkoxy and $C_3$-$C_8$ cycloalkyl; or (ii) aryl or heteroaryl optionally substituted with from 1 to 3 substituents independently chosen from halogen, $C_1$-$C_6$ alkyl, $C_1$-$C_6$ alkoxy, $CF_3$, $OCF_3$. Radical, $R_{13}$ is independently chosen from H, $C_1$-$C_6$ alkyl and $(CH_2)_n$—$C_3$-$C_8$ cycloalkyl; and radical, $R_{14}$ is independently chosen from H, $C_1$-$C_6$alkyl and CO—($C_1$-$C_6$alkyl).

Alternatively, $R_{13}$ and $R_{14}$ when taken together with the nitrogen to which they are bonded form a 5-6 membered heterocyclyl; wherein p is an integer from 1 to 3, and each instance of n is independently selected from 0 and an integer from 1 to 3; and provided that when A is $SO_2$ and $R_5$ is hydrogen, then $R_6$ is not aryl or heteroaryl.

Prodrugs, stereoisomers, mixtures of stereoisomers, racemates, salts, hydrates, solvates, salt hydrates, acid salt hydrates, and isomorphic crystalline forms of the compounds of having the structure of formula I are also contemplated within the scope of the present invention.

The compounds of the present invention have been shown to bind one or more cannabinoid receptors on the surface of mammalian cells and to modulate intracellular cyclic AMP (cAMP) concentration in these cells. Cannabinoid receptors include for instance and without limitation, cannabinoid receptors CB1 and CB2.

The compounds of the present invention include agonists, partial agonists and inverse agonists acting at a cannabinoid receptor, such as the CB2 receptor. In particular embodiments the compounds of the present invention exhibit selectivity for the CB2 receptor over the CB1 receptor.

The invention also provides pharmaceutical compositions that include a compound having the structure of formula I or a prodrug, stereoisomer, mixture of stereoisomers, racemate, salt, hydrate, solvate, acid salt hydrate, or an isomorphic crystalline form thereof, and a pharmaceutically acceptable carrier or excipient.

The invention further provides a method of preventing, inhibiting or treating a cannabinoid receptor-associated disease or condition in a mammal. The method includes administering to a mammal in need thereof an effective amount of a compound having the structure of formula I, or a prodrug, stereoisomer, mixture of stereoisomers, racemate, salt, hydrate, solvate, salt hydrate, acid salt hydrate, or an isomorphic crystalline form thereof.

DETAILED DESCRIPTION

The following definitions provide the meaning of the listed terms as used herein:

The term "alkyl" means a saturated branched or straight chain monovalent hydrocarbon radical of up to about 6 carbon atoms. Thus, the term alkyl includes saturated straight and branched carbon atom chains, for example: methyl, ethyl, propyl, isopropyl, n-butyl, iso-butyl, sec-butyl, t-butyl, pentyl, isopentyl, neopentyl, tert-pentyl, and so on. A chain of one to six carbon atoms is interchangeably designated herein as $C_1$-$C_6$ alkyl; a chain of three to six carbon atoms is also referred to as $C_3$-$C_6$ alkyl and so forth. Each designation of an alkyl group in this application, unless otherwise specified, can be substituted with from one to three radicals independently selected from hydroxy, halogen and amino.

The term "alkoxy" refers to an —Oalkyl substituent group wherein the alkyl group is as defined above. The term "$C_3$-$C_6$ alkyloxyalkyl" refers to an alkyl radical bonded through an oxygen atom to a second alkyl radical, wherein the total number of carbon atoms in the alkyloxyalkyl can be from 3 to 6, and wherein the alkyl radicals can be branched or straight chains as defined above.

The term "cycloalkyl" means a saturated or partially unsaturated monocyclic, polycyclic or bridged hydrocarbon ring system radical or linking group. A ring of from three to ten carbon atoms is interchangeably designated as $C_3$-$C_{10}$ cycloalkyl; a ring of three to seven carbon atoms is designated by $C_3$-$C_7$ cycloalkyl and so forth. Cycloalkyl as used herein includes, but is not limited to such groups as adamantyl, cyclopropyl, cyclobutyl, cyclopentyl, cyclohexyl, cyclohexenyl, cycloheptyl, cyclooctyl and bridged bicyclyl, such as for instance and without limitation, 1,3,3-trimethylbicyclo-[2.2.1]heptyl. Each cycloalkyl can include from one to three substituent groups selected from alkyl, alkoxy, hydroxyl, amino and alkylamino.

The term "heterocyclyl" means a saturated, partially unsaturated or unsaturated monocyclic, polycyclic or bridged hydrocarbon ring, ring system radical or linking group, wherein at least one ring carbon atom has been replaced with one or more heteroatoms independently selected from N, O, or S. In addition, the sulfur atom can be in the S, SO or $SO_2$ oxidation state. A heterocyclyl radical as used herein further includes ring systems having up to 4 nitrogen atom ring members or a ring system having an oxygen or sulfur atom ring member and optionally one or more nitrogen atoms in the heterocyclyl ring.

The term "heterocyclyl" as used herein also includes heterocyclic ring systems that have more than one ring, wherein the additional ring or rings can, but need not necessarily, include one or more heteroatoms. Each heterocyclyl can be attached through a carbon or nitrogen atom of the heterocyclic system and in addition each ring hydrogen can be optionally substituted with a radical such as for instance and without limitation, alkyl, alkoxy, amino, dialkylamino, alkylcarboxyl and arylalkylcarboxyl. The term "heterocyclyl" also includes "heteroaryl" moieties.

As used herein the term "Unsubsituted heterocyclyl" includes, but is not limited to such groups as, for instance, furyl, thienyl, pyrrolinyl, pyrrolidinyl, pyrrolyl, oxazolyl, thiazolyl, imidazolyl, imidazolinyl, imidazolidinyl, pyrazolinyl, pyrazolidinyl, pyrazolyl, oxadiazolyl, triazolyl, thiadiazolyl, tetrazolyl, pyranyl, pyridinyl, piperidinyl, dioxanyl, morpholinyl and thiomorpholinyl.

The term "aryl" refers to an unsaturated, π-electron conjugated monocyclic or polycyclic hydrocarbon ring system radical of six, ten or fourteen carbon atoms. An aryl radical is derived by the removal of one hydrogen atom from a single carbon ring atom. Aryl includes, but is not limited to, phenyl, naphthalenyl, azulenyl, anthracenyl and can be optionally substituted with a radical such as for instance and without limitation, alkyl, alkoxy, hydroxy, amino, alkylamino and halogen.

The term "heteroaryl" is used interchangeably with the term "unsaturated heterocyclyl" and refers to an aromatic heterocycle such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, and can be optionally substituted with a radical such as for instance and without limitation, alkyl, alkoxy, hydroxyl, amino, alkylamino or halogen.

The term "alkylaryl" refers to an optionally substituted aryl group attached to a carbon atom of an alkyl group. Alkylaryl includes, for example, benzyl, phenethyl, phenylpropyl and phenylbutyl.

The term "alkylheteroaryl" refers to an optionally substituted heteroaryl group attached to a carbon atom of an alkyl group. The term "alkylcarboxyl" means a radical of the formula —COO($CH_2$)$_n$$CH_3$. The term "arylcarboxyl" means a radical of the formula —COOaryl, wherein aryl is as defined above. The term "arylalkylcarboxyl" means a radical of the formula —COO($CH_2$)$_p$aryl, wherein aryl is as defined above.

The following terms that are also used throughout this application are defined as follows: "Halogen" means fluoro, chloro, bromo or iodo. "Carboxyl" means a radical of the formula —COOH. "Hydroxyl" means a radical of the formula —OH. "Cyano" means a radical of the formula —C≡N. "Amino" means a radical of the formula —$NH_2$ or a linking group of the formula —NH—. "Amido" refers to one of —CONH2, —CONH—, —NHCO— and —NH-COOH. "Alkylamino" means a radical of the formula —NH-alkyl or —N(alkyl)$_2$; dialkylamino means an amino radical substituted with two alkyl groups where the alkyl groups may be the same or different. The term "solvates" describes a complex wherein the compound is coordinated with a proportional amount of a solvent molecule. Specific solvates wherein the solvent is water are also referred to as hydrates.

The present invention provides compounds having the structure of formula I:

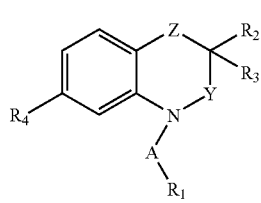

and prodrugs, stereoisomers, racemates, salts, hydrates, solvates, salt hydrates, acid salt hydrates and isomorphic crystalline forms thereof, wherein:

A is CO, CONH, or $SO_2$; Y is $(CH_2)_p$; and Z is S, SO, $SO_2$ or O.

$R_1$ is (i) $C_1$-$C_6$ alkyl; (ii) aryl optionally substituted with from 1 to 3 substituents independently selected from group consisting of halogen, $C_1$-$C_6$ alkyl, $CF_3$, $OCF_3$, $OR_{10}$, $COR_{10}$, $COOR_{10}$, $NR_{10}R_{11}$, $CONR_{10}R_{11}$; (iii) $C_3$-$C_8$ cycloalkyl; or (iv) 4- to 10-membered heterocyclyl, optionally substituted with from 1 to 3 substituents independently chosen from halogen, $C_1$-$C_6$ alkyl, $C_1$-$C_6$ alkoxy, $CF_3$, $OCF_3$, $OR_{10}$, $COOR_{10}$, $NR_{10}R_{11}$, $COR_{10}$, and $CONR_{10}R_{11}$. $R_2$ and $R_3$ are each independently H or $C_1$-$C_3$ alkyl.

$R_4$ is (i) $COOR_5$; (ii) $CONR_5R_6$; (iii) aryl optionally substituted with from 1 to 3 substituents independently chosen from halogen, $C_1$-$C_6$ alkyl, $C_1$-$C_6$ alkoxy, $CF_3$ and $OCF_3$; or (iv) 5- to 10-membered heterocyclyl optionally substituted with from 1 to 3 substituents independently chosen from halogen, $CF_3$, $OCF_3$ and $R_{12}$.

$R_5$ and $R_6$ are each independently chosen from, H, $C_1$-$C_6$ alkyl, $C_1$-$C_6$ alkoxyalkyl, $(CH_2)_n$-aryl, $(CH_2)_n$—$C_3$-$C_{10}$ cycloalkyl and $(CH_2)_n$ (3- to 8-membered heterocyclyl); or $R_5$ is H, or $C_1$-$C_6$ alkyl and $R_6$ is chosen from $CR_7R_8R_9$ and —$NHCOR_{12}$. Alternatively, $R_5$ and $R_6$ taken together with the nitrogen atom to which they are bonded form a 4- to 10-membered heterocyclyl optionally substituted with from 1 to 3 substituents independently chosen from halogen, $C_1$-$C_6$ alkyl, $C_1$-$C_6$ alkoxy, $CF_3$, $OCF_3$, $OR_{10}$, $COOR_{10}$, $NR_{10}R_{11}$, $COR_{10}$, and $CONR_{10}R_{11}$.

$R_7$ and $R_8$ are each independently chosen from H and $C_1$-$C_6$ alkyl.

Alternatively, $R_7$ and $R_8$ taken together with the carbon atom to which they are bonded form a 3- to 6-membered carbocyclyl group or a 3- to 6-membered heterocycyl.

The group $R_9$ is chosen from $(CH_2)_p$—$OR_{13}$, $(CH_2)_p$—$NR_{13}R_{14}$, $(CH_2)_nCOOR_{13}$, and $(CH_2)_nCONR_{13}R_{14}$.

$R_{10}$ is (i) independently chosen from H, $C_1$-$C_6$ alkyl and $(CH_2)_n$—$C_3$-$C_8$ cycloalkyl; or (ii) aryl or heteroaryl optionally substituted with from 1 to 3 substituents independently chosen from, halogen, $CF_3$, $OCF_3$, $C_1$-$C_6$ alkyl, $C_1$-$C_6$ alkoxy.

$R_{11}$ is independently chosen from H, $C_1$-$C_6$alkyl and CO—($C_1$-$C_6$alkyl).

Alternatively, $R_{10}$ and $R_{11}$ when taken together with the nitrogen to which they are bonded form a 5-6 membered heterocyclyl.

$R_{12}$ is (i) chosen from $C_1$-$C_6$ alkyl, $C_1$-$C_6$ alkoxy and $C_3$-$C_8$ cycloalkyl; or (ii) aryl or heteroaryl optionally substituted with from 1 to 3 substituents independently chosen from halogen, $C_1$-$C_6$ alkyl, $C_1$-$C_6$ alkoxy, $CF_3$, $OCF_3$.

$R_{13}$ is independently chosen from H, $C_1$-$C_6$ alkyl and $(CH_2)_n$—$C_3$-$C_8$ cycloalkyl; and $R_{14}$ is independently chosen from H, $C_1$-$C_6$alkyl and CO—($C_1$-$C_6$alkyl).

Alternatively, $R_{13}$ and $R_{14}$ when taken together with the nitrogen to which they are bonded form a 5-6 membered heterocyclyl; wherein p is an integer from 1 to 3, and each instance of n is independently selected from 0 and an integer from 1 to 3; and provided that when A is $SO_2$ and $R_5$ is hydrogen, then $R_6$ is not aryl or heteroaryl, substituted aryl or substituted heteroaryl.

In one embodiment of the present invention, the compounds have the structure of formula I, in which Z is S or $SO_2$; Y is $CH_2$; and $R_2$ and $R_3$ are each independently H or $CH_3$. In another embodiment, Z is O; Y is $CH_2$; and $R_2$ and $R_3$ are each independently H or $CH_3$. In still another embodiment, Z is S or $SO_2$; Y is $CH_2CH_2$; and $R_2$ and $R_3$ are each independently H or $CH_3$. In yet another embodiment, Z is O; Y is $CH_2CH_2$; and $R_2$ and $R_3$ are each independently H or $CH_3$. Additionally, in another embodiment, of the present invention, the compounds have the structure of formula I, in which A is CO or $SO_2$.

In a particular embodiment of the compounds of formula I, $R_1$ is chosen from the following four groups: (i) $C_1$-$C_6$ alkyl; (ii) aryl optionally substituted with from 1 to 3 substituents independently selected from group consisting of halogen, $C_1$-$C_6$ alkyl, $CF_3$, $OCF_3$, $OR_{10}$, $COR_{10}$, and $COOR_{10}$; (iii) $C_3$-$C_8$ cycloalkyl; and (iv) 4- to 10-membered heterocyclyl, optionally substituted with from 1 to 3 substituents independently chosen from halogen, $C_1$-$C_6$ alkyl, $C_1$-$C_6$ alkoxy, $CF_3$, and $OCF_3$. The radical $R_4$ is (i) $CONR_5R_6$, or (ii) 5- to 10-membered heterocyclyl optionally substituted with from 1 to 3 substituents independently chosen from halogen, $CF_3$, $OCF_3$, and $R_{12}$; and $R_5$ and $R_6$ are defined by one of the following three groups: (i) $R_5$ and $R_6$ are each independently selected from the group consisting of H, $C_1$-$C_6$ alkyl, $C_1$-$C_6$ alkoxyalkyl, $(CH_2)_n$—$C_3$-$C_{10}$ cycloalkyl, and $(CH_2)_n$ (3- to 8-membered heterocyclyl); (ii) $R_5$ is H or $C_1$-$C_6$ alkyl, and $R_6$ is $CHR_8R_9$ or —$NHCOR_{12}$; and (iii) $R_5$ and $R_6$, taken together with the nitrogen atom to which they are bonded, form a 4- to 10-membered heterocyclyl optionally substituted with from 1 to 3 substituents independently selected from the group consisting of halogen, $C_1$-$C_6$ alkyl, $C_1$-$C_6$ alkoxy, $CF_3$, $OCF_3$, $OR_{10}$, $COOR_{10}$, $NR_{10}R_{11}$, $COR_{10}$, and $CONR_{10}R_{11}$.

In certain embodiments of the compounds of formula I, $R_1$ is $C_1$-$C_3$ alkyl, aryl, $C_1$-$C_3$ alkylaryl, haloaryl, or $C_1$-$C_3$ alkoxyaryl; and $R_2$ and $R_3$ are either both H, or both $CH_3$. In particular embodiments of these compounds, each aryl moiety of aryl or substituted aryl is independently phenyl, naphthalenyl, or azulenyl; and each heterocyclyl moiety of a heterocyclyl or substituted heterocyclyl is independently a five-, six-, seven- or eight-membered saturated, partially saturated or heteroaromatic ring containing 1, 2 or 3 heteroatoms independently chosen from N, O and S.

In certain other embodiments of the compounds of formula I, $R_1$ is (i) $C_1$-$C_6$ alkyl; (ii) aryl optionally substituted with from 1 to 3 substituents independently selected from group consisting of halogen, $C_1$-$C_6$ alkyl, $CF_3$, $OCF_3$, $OR_{10}$, $COR_{10}$, and $COOR_{10}$; (iii) $C_3$-$C_8$ cycloalkyl; or (iv) 4- to 10-membered heterocyclyl, optionally substituted with from 1 to 3 substituents independently selected from the group consisting of halogen, $C_1$-$C_6$ alkyl, $C_1$-$C_6$ alkoxy, $CF_3$, and $OCF_3$.

In other embodiments, the compounds have the structure of formula I, in which $R_2$ and $R_3$ are either both H, or both $CH_3$; and $R_4$ is $CONR_5R_6$; wherein $R_5$ and $R_6$ are each independently, H, $C_1$-$C_6$ alkyl, or $(CH_2)_n$—$C_3$-$C_{10}$ cycloalkyl.

In further embodiments, the compounds have the structure of formula I, in which $R_2$ and $R_3$ are both hydrogen or $C_1$-$C_3$ alkyl. In particular embodiments, $R_2$ and $R_3$ are both hydrogen or $CH_3$; and $R_5$ is hydrogen.

In still other embodiments, the compounds have the structure of formula I, in which $R_4$ is (i) $CONR_5R_6$, or (ii) a 5-, 6-, 7-, 8-, 9- or 10-membered heterocyclyl optionally substituted with from 1 to 3 substituents independently chosen from halogen, $CF_3$, $OCF_3$, and $R_{12}$, wherein $R_5$, $R_6$ and $R_{12}$ are as defined above.

In still further embodiments, the compounds have the structure of formula I, in which $R_5$ and $R_6$ are defined by one of the following: (i) $R_5$ and $R_6$ are each independently selected from the group consisting of H, $C_1$-$C_6$ alkyl, $C_1$-$C_6$ alkoxyalkyl, $(CH_2)_n$—$C_3$-$C_{10}$ cycloalkyl, and $(CH_2)_n$ (3- to 8-membered heterocyclyl); or (ii) $R_5$ is H or $C_1$-$C_6$ alkyl, and $R_6$ is $CHR_8R_9$ or —$NHCOR_{12}$; or (iii) $R_5$ and $R_6$, taken together with the nitrogen atom to which they are bonded, form a 4- to 10-membered heterocyclyl optionally substituted with from 1 to 3 substituents independently selected from the group consisting of halogen, $C_1$-$C_6$ alkyl, $C_1$-$C_6$ alkoxy, $CF_3$, $OCF_3$, $OR_{10}$, $COOR_{10}$, $NR_{10}R_{11}$, $COR_{10}$, and $CONR_{10}R_{11}$, wherein $R_8$, $R_9$, $R_{10}$, $R_{11}$, $R_{12}$ and n are each as defined above.

In certain embodiments, the compounds of the present invention have the structure of formula I, in which $R_1$ is $C_1$-$C_3$ alkyl, aryl, $C_1$-$C_3$ alkylaryl, haloaryl, or $C_1$-$C_3$ alkoxyaryl; and $R_4$ is $CONR_5R_6$; and $R_5$ and $R_6$ are each independently, H, $C_1$-$C_4$ alkyl, $C_1$-$C_4$ alkoxyalkyl, or $(CH_2)_nC_3$-$C_8$ cycloalkyl. In particular embodiments of these compounds, each aryl moiety of aryl or substituted aryl is independently phenyl, naphthalenyl, azulenyl or anthracenyl; and wherein each heterocyclyl moiety of a heterocyclyl or substituted heterocyclyl is independently a five- to eight-membered saturated, partially saturated or heteroaromatic ring containing 1, 2 or 3 heteroatoms, each heteroatom being independently chosen from N, O and S.

In some embodiments, the compounds of the present invention have the structure of formula I, in which A is $SO_2$;

Z is S; $R_1$ is $C_1$-$C_6$ alkyl, aryl, $C_1$-$C_6$ alkylaryl, haloaryl, aryl$CF_3$, arylO$CF_3$ or $C_1$-$C_6$ alkoxyaryl; $R_2$ and $R_3$ are each independently H or $CH_3$; and $R_4$ is $CONR_5R_6$; and $R_5$ and $R_6$ are each independently, H, $C_1$-$C_6$ alkyl, or $(CH_2)_n C_3$-$C_{10}$ cycloalkyl. In particular embodiments of these compounds, $R_1$ is $C_1$-$C_3$ alkyl, aryl, $C_1$-$C_3$ alkylaryl, haloaryl, or $C_1$-$C_3$ alkoxyaryl. In other particular embodiments of these compounds, $R_2$ and $R_3$ are either both H, or both $CH_3$. In still other particular embodiments of these compounds, $R_4$ is $CONR_5R_6$; and $R_5$ and $R_6$ are each independently, H, $C_1$-$C_6$ alkyl or $C_3$-$C_{10}$ cycloalkyl.

In another embodiment, the compounds of the invention conform to the structure of formula I, provided that when A is $SO_2$ and $R_5$ is H, then $R_6$ is not aryl or heteroaryl. In still other embodiments, when A is $SO_2$ and $R_5$ is H, then $R_6$ is not substituted aryl or substituted heteroaryl.

In certain embodiments the compounds of the present invention bind one or more cannabinoid receptors such as, without limitation the CB1 receptor or the CB2 receptor. The cannabinoid receptors are generally defined as the group of G protein-coupled receptors that bind a well-known group of substances that are structurally related to Δ9-tetrahydrocannabinol (THC).

In certain embodiments, the compounds of the present invention exhibit an $EC_{50}$ for the CB2 receptor in a range of from about 0.01 nM to about 10 μM. In other embodiments, the compounds exhibit an $EC_{50}$ for the CB2 receptor of from about 0.01 nM to about 1 μM. In particular embodiments, the compounds exhibit an $EC_{50}$ for the CB2 receptor of from about 0.1 nM to about 100 nM.

In this specification, salts of a compound of formula I refers to a complex of the compound with an inorganic or organic counter ion or counter ions. For examples, see Handbook of Pharmaceutical Salts: Properties, Selection and Use; Stahl P. H., Wermuth, C. G., Eds.; John Wiley and Sons, 2002. Pharmaceutically useful salts include those obtained by treating the compound, functioning as a base, with an inorganic or organic acid to form a salt or salts. Additional pharmaceutically useful salts include those obtained by treating the compound, functioning as an acid, with an inorganic or organic base to form a salt or salts. Other pharmaceutically useful salts include those obtained by treatment of basic nitrogen-containing groups with such agents as alkyl halides (such as chlorides or bromides) to form a quaternary ammonium a salt or salts.

In certain embodiments, the compounds of the present invention are useful as therapeutic and/or prophylactic agents for the treatment or prevention of a cannabinoid-associated disease or condition. An effective amount of the compound, prodrug, stereoisomer, racemate, salt, hydrate, solvate, acid salt hydrate, or an isomorphic crystalline form of a compound of the present invention can be administered to a mammal in need of such treatment or prophylaxis in order to manage, ameliorate, treat, cure or prevent such a disease or condition. The term "cannabinoid-associated disease or condition" as used herein means a disease or condition that is treatable by therapeutic compounds that act directly or indirectly on a cannabinoid receptor. In particular embodiments, the compounds of the present invention are useful as therapeutic and/or prophylactic agents for the treatment or prevention of a CB2-associated disease or condition. These compounds can be administered to a mammal in need of such treatment or prophylaxis in order to manage, ameliorate, treat, cure or prevent a CB2-associated disease or condition. The term "CB2-associated disease or condition" as used herein means a disease or condition that is treatable by therapeutic compounds that act directly or indirectly on the CB2 receptor.

Such cannabinoid-associated disease or conditions that can be managed, ameliorated, treated, inhibited, cured or prevented by administration of compounds or pharmaceutical compositions of the present invention include, but are not limited to: pain, inflammation and pruritis (itching).

The compounds and pharmaceutical compositions of the present invention can be administered to treat or prevent pain of a variety of origins, such as inflammatory pain, visceral pain, postoperative pain, metastatic cancer pain, breakthrough cancer pain, neuropathic pain, musculoskeletal pain, dysmenorrhea (menstrual pain), migraine and headache. Neuropathic pain includes pain due to diabetic neuropathy, fibromyalgia, lower back pain, sciatica, and pain from physical trauma, cancer, amputation, toxins or chronic inflammatory conditions. Other forms of pain preventable or treatable by compounds and pharmaceutical compositions of the present invention include, for instance, virally-induced pain, chemotherapy-induced pain, somatic pain, cutaneous pain, ocular/otitic pain and gastrointestinal pain.

The compounds and pharmaceutical compositions of the present invention are also useful for the treatment and prevention of inflammatory diseases and conditions. These include for instance, inflammation due to rheumatoid arthritis, systemic lupus erythematosus, Crohn's disease, psoriasis, eczema, multiple sclerosis, diabetes and thyroiditis, as well as ocular and otic inflammation.

The compounds and pharmaceutical compositions of the present invention are also useful in the treatment and prevention of pruritis. The pruritis may be due to atopic dermatitis, eczema, or insect bites. Other forms of pruritis treatable or preventable by the compounds and pharmaceutical compositions of the present invention include ocular and/or otic pruritis, kidney dialysis-induced pruritis and opioid-induced pruritis.

The compounds and pharmaceutical compositions of the present invention are also useful in the treatment and prevention of skin disorders (e.g. sunburn, dermatitis, pruritis); lung disorders (e.g. chronic obstructive pulmonary disease, cough, asthma, bronchitis); ophthalmic disorders (e.g. glaucoma, retinitis, reinopathies, uveitis, conjunctivitis); gastrointestinal disorders (e.g. ulcerative colitis, irritable bowel syndrome, coeliac disease, inflammatory bowel disease, gastroesophageal reflux disease, organ transplant, nausea, emesis); cardiovascular disorders (e.g. stroke, cardiac arrest, atherosclerosis, myocardial ischemia); neurodegenerative, neuroinflammatory or psychiatric disorders (e.g. senile dementia, Alzheimer's disease, vascular dementia, amyotrophic lateral sclerosis, neuroinflammation, tinnitus); bladder disorders (e.g. bladder hyper-reflexia, cystitis) and cancer, such as for instance, lymphoblastic leukemia and lymphoma, acute myelogenous leukemia, chronic lymphocytic leukemia, glioma, skin cancer, breast cancer, prostate cancer, liver cancer, kidney cancer, lung cancer, pancreatic cancer.

In addition, compounds and pharmaceutical compositions of the present invention can be used to modulate bone formation and/or resorption for treating certain conditions including, but not limited to, ankylosing spondylitis, gout, arthritis associated with gout, osteoarthritis and osteoporosis.

The compounds of the present invention can be administered as pharmaceutical compositions in readily available formulations in solid or liquid form. Solid formulations can include optional inactive fillers, carriers or diluents and can be formed into tablets or encapsulated for oral delivery. Liquid formulations include solutions, suspensions and slurries suitable for oral, topical or parenteral routes of administration.

The compounds and pharmaceutical compositions of the present invention can be delivered by any of the standard routes, for example orally, parentarally, sublingually, dermally, transdermally, rectally, via inhalation, or by buccal, nasal, ocular or otic administration.

ABBREVIATIONS

AcOH acetic acid
Burgess reagent methyl N-(triethylammoniumsulphonyl) carbamate
° C. degrees Celsius
d doublet
DCM dichloromethane
DCE 1,2-dichloroethane
DIPEA diisopropylethyl amine
DMAP 4-(N,N-dimethylamino)pyridine
DMF N,N-dimethylformamide
EDCI 1-ethyl-3-(3'-dimethylaminopropyl)carbodiimide
EtOAc ethyl acetate
ESCI electron spray/chemical ionization
g grams
$^1$H NMR proton nuclear magnetic resonance
HCl hydrochloric acid
HOBt 1-hydroxybenzotriazole
HPLC high performance liquid chromatography
J coupling constant (NMR spectroscopy)
$K_3PO_4$ potassium phosphate
L liter
LCMS Liquid Chromatography Mass Spectroscopy
LiOH lithium hydroxide
M mol.L$^{-1}$ (molar)
m multiplet
m/z mass-to-charge ratio
mCPBA m-Chloroperoxybenzoic acid
MeOH methanol
mg milligrams
MHz megahertz
min minute, minutes
µL microliter
mL milliliter
mol mole
mmol millimoles
µmol micromole
MS mass spectrum, mass spectrometry
N equiv L$^{-1}$ (normal)
$NaHCO_3$ sodium bicarbonate
NaI sodium iodide
NaOH sodium hydroxide
$Na_2SO_4$ sodium sulfate
nM nanomolar
NMR Nuclear Magnetic Resonance
NUC Nucleophile
$PdCl_2$(dppf) Palladium[1,1-bis(diphenyphosphino)ferrocene]dichloride Pd(PPh$_3$)$_4$tetrakis-triphenylphosphine palladium(0)
pH negative logarithm of hydrogen ion concentration
$POCl_3$ phosphoryl trichloride
$PPh_3Cl_2$ dichloro(triphenyl)phosphorane
q quartet
s singlet
$SOCl_2$ thionyl chloride
t triplet
TBAF tetrabutylammonium fluoride
TBAI tetrabutylammonium iodide
TBTU O-(benzotriazol-1-yl)-N,N,N',N'-tetramethyluronium tetrafluoroborate
THF tetrahydrofuran
TLC thin layer chromatography
TMS tetramethylsilane
UPLC ultra performance liquid chromatography General Methods All reactions involving moisture sensitive compounds were carried out under an anhydrous nitrogen or argon atmosphere. All reagents were purchased from commercial sources and used without further purification. Unless otherwise noted, the starting materials used in the examples were obtained from readily available commercial sources or synthesized by standard methods known to those skilled in the art of organic synthesis. Normal phase chromatography and reverse phase chromatography was performed on an ISCO CombiFlash Companion.

Compounds were characterized by their HPLC-Electrospray/chemical ionization mass spectra (HPLC ESCI-MS) on a Waters HPLC-MS system (Waters Corp., Milford, Mass.) equipped with a 2767 Sample Manager, 2545 Binary Gradient Module, SFO System Fluidics Organizer, 2996 Photodiode Array Detector and 3100 Mass Detector. Data was collected across a range of wavelengths from 220 nm to 280 nm and in positive ESCI mode. Spectra were scanned from 100-1400 atomic mass units. The HPLC column was a Waters XBridge C18 3.5 um 4.6×30 mm; eluents were A: water with 0.1% formic acid and B: acetonitrile with 0.1% formic acid. Gradient elution was from 5% B to 95% B over 2.3 minutes with an initial hold of 0.2 minutes and a final hold at 95% B of 0.5 minutes. Total run time was 4 minutes.

Ultra performance liquid chromatography—electrospray/chemical ionization mass spectra (UPLC ESCI-MS) for characterization were obtained using a Waters (Waters Corporation, Milford, Mass.) UPLC-MS system equipped with an Acquity Sample Manager, Acquity Binary Solvent Manager, Acquity Photodiode Array Detector, Acquity Evaporative Light Scattering Detector and SQ Detector. Data was collected at distinct wavelengths of 220 nm and 254 nm and in positive electrospray-chemical ionization mode. The UPLC column used was a Waters Acquity UPLC BEH C18 1.7 um 2.1×50 mm. Spectra were scanned from 100-1400 atomic mass units. The eluents were A: water with 0.1% formic acid and B: acetonitrile with 0.1% formic acid. Gradient elution from 5% B to 95% B over 0.8 minutes was used with a final hold at 95% B of 0.2 minutes at a flow rate of 0.8 milliliters per minute. Total run time was 1.5 minutes.

Nuclear magnetic resonance spectra were recorded using either a Bruker Avance spectrometer (DPX400 Shielded) or a Jeol ECX 400 MHz spectrometer. Spectra were acquired in the indicated solvent. Chemical shifts (δ) are given in ppm (parts per million upfield or downfield from TMS defined as 0 ppm). Coupling constants J are in hertz (Hz). Peak shapes in the NMR spectra are indicated by symbols 'q' (quartet), 't' (triplet), 'd' (doublet), 's' (singlet), 'br s' (broad singlet), 'br' (broad) 'm' (multiplet) and 'br d' (broad doublet).

Synthetic Schemes

Many of the compounds of the present invention can be prepared according to the non-limiting synthetic schemes outlined in the general Schemes 1-5 shown below.

Compounds of Formula I can be readily synthesized from intermediate 1-7. One method for the preparation of intermediate 1-7 is shown in scheme 1. Nucleophilic aromatic substitution of 4-fluoro-3-nitrobenzoic acid (1-1) is effected by treatment of 1-1 with a nucleophile 1-2 (Z=S) in polar aprotic solvents such as, for instance, DMF, in the presence of a base such as an inorganic carbonate. Bis-chlorination of intermediate 1-3 is performed with a chlorinating reagent, such as $SOCl_2$ in an aprotic solvent, such as toluene or 1,2-dichloroethane at elevated temperatures (such as, for instance, at 70° C.). For generation of amide intermediates 1-5 (NUC=$NR_5R_6$), bis-chloride 1-4 is treated with a primary or secondary amine in DCM in the presence of an aqueous bicarbonate solution. For generation of ester intermediates 1-5 (NUC=$OR_5$), bis-chloride 1-4 is treated with the alcohol in the presence of a tertiary amine base with or without the presence of a co-solvent such as dichloromethane. Aniline 1-6 is readily obtained by reduction of the nitro moiety in intermediate 1-5. Reduction occurs under a variety of metal mediated conditions including but not limited to iron in acidic media, palladium-catalyzed hydrogenation and tin(II) chloride in alcoholic solvents. Finally, intermediate 1-7 can be isolated by the cyclization of intermediate 1-6 by treatment with an iodide source such as NaI in an appropriate aprotic solvent such as 2-butanone at an elevated temperature, such as for instance, at 70° C.

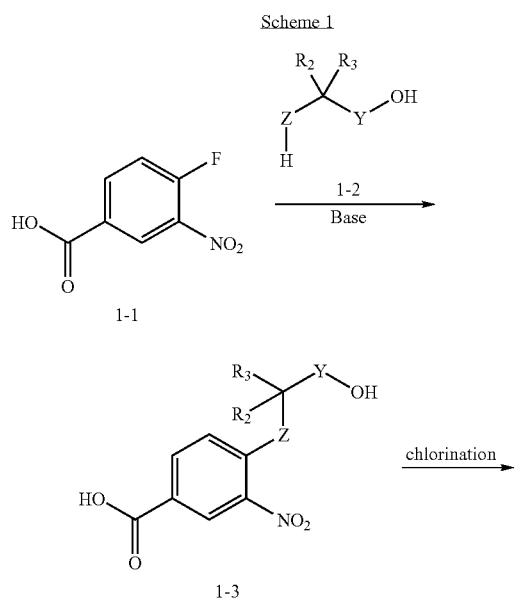

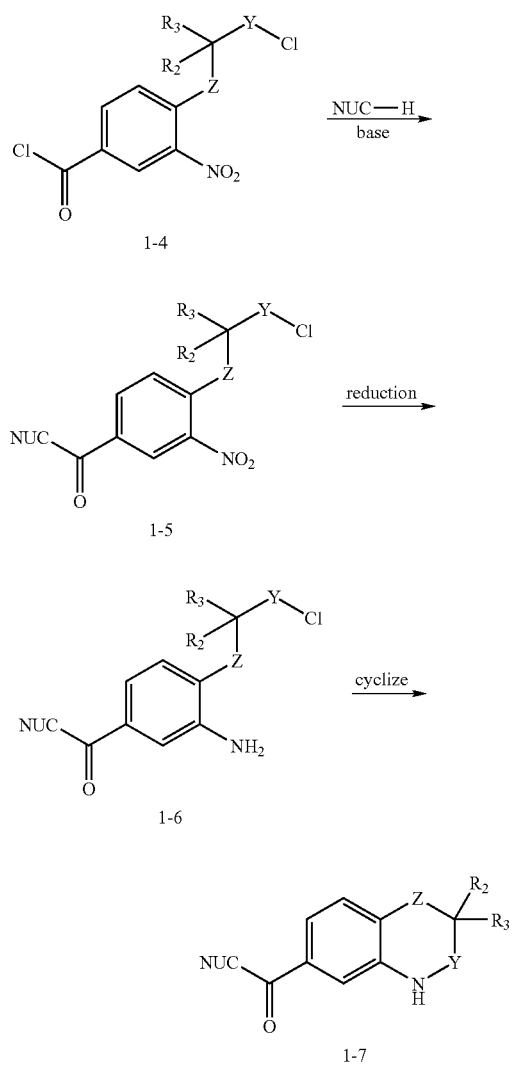

NUC—H = $HOR_5$ or $HNR_5R_6$

Intermediate 1-7 can be used to complete the synthesis of the compound of formula Ia as depicted in Scheme 2. For examples where NUC=$NR_5R_6$, synthesis of compounds of formula Ia can be accomplished in a single step coupling with an acid halide, sulfonyl halide or acid anhydride, 2-1 in which X is a halogen, an alkylcarboxyl or an arylcarboxyl in dichloromethane in the presence of an appropriate base, such as an aqueous inorganic bicarbonate, or a tertiary amine base and/or DMAP.

Additionally compounds of formula Ia can also be derived from compound 1-7 via a three step process. Compound 1-7 (with NUC=$OR_5$) is treated with an acid halide, sulfonyl halide or acid anhydride, 2-1 in which X is a halogen, an alkylcarboxyl or an arylcarboxyl in dichloromethane in the presence of an appropriate base, such as an aqueous inorganic bicarbonate, or a tertiary amine base and/or DMAP to provide compound 2-2.

Scheme 2

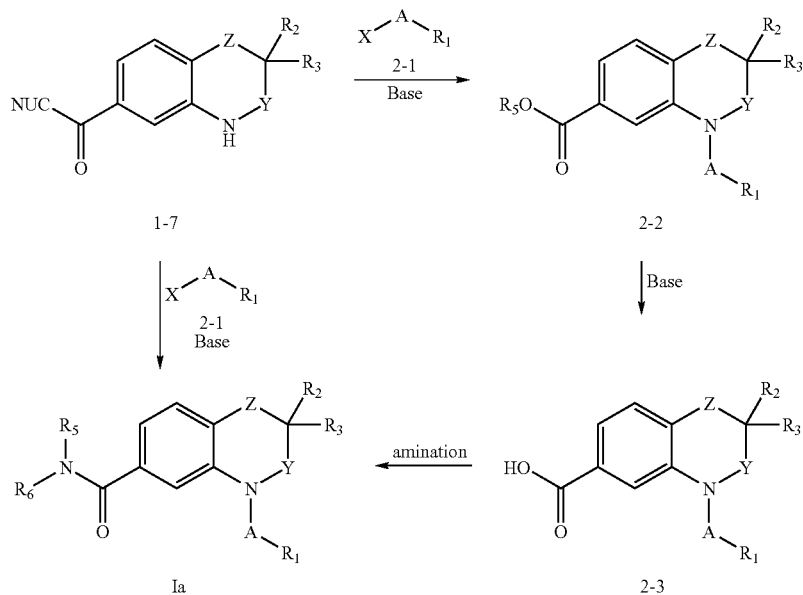

Hydrolysis of compounds 2-2 with aqueous bases such as LiOH is performed in mixtures of protic and aprotic solvents such as THF and MeOH. The resulting acid can be directly transformed to yield the amide by traditional peptide coupling conditions (e.g. EDCI, HOBt) or by generation of the acid chloride as described above for intermediated 1-4, followed by amination as described above for intermediates 1-5 (where the nucleophile, NUC corresponds to $NR_5R_6$ of the compounds of formula I).

Scheme 3

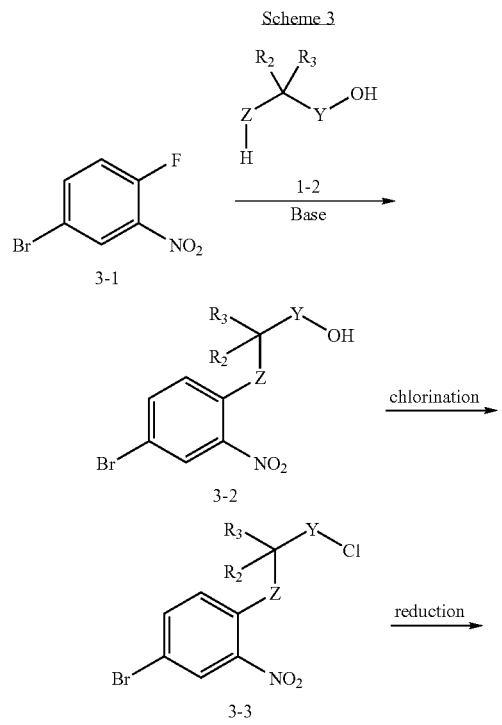

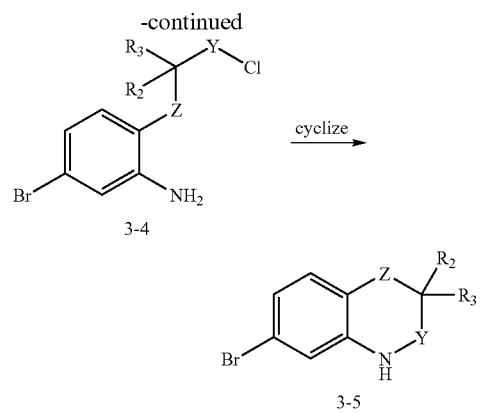

Compounds of formula Ib wherein $R_4$ is an aryl or heterocyclyl group can be prepared by the methods described in the general synthetic schemes 3 and 4 described below. For instance, one method for the preparation of intermediate 3-5 begins with 4-bromo-1-fluoro-2-nitrobenzene (3-1).

Nucleophilic aromatic substitution can be effected by treatment of 3-1 with the appropriate nucleophile (1-2, wherein Z=S) in a polar aprotic solvent such as DMF in the presence of a base, such as an inorganic carbonate. Chlorination of intermediate 3-2 is performed with a reagent such as $SOCl_2$ in an aprotic solvent such as toluene or 1,2-dichloroethane at elevated temperatures (such as, for instance, 70° C.). The aniline 3-4 can be readily obtained by reduction of the nitro moiety of intermediate 3-3. Reduction occurs under a variety of metal-mediated conditions, including but not limited to iron in acidic media, palladium-catalyzed hydrogenation and tin(II) chloride in an alcoholic solvent. Finally, intermediate 3-5 is isolated by the cyclization of intermediate 3-4 by treatment with an iodide source such as NaI in an appropriate aprotic solvent such as 2-butanone at an elevated temperature, such as for instance, at 70° C.

Scheme 4

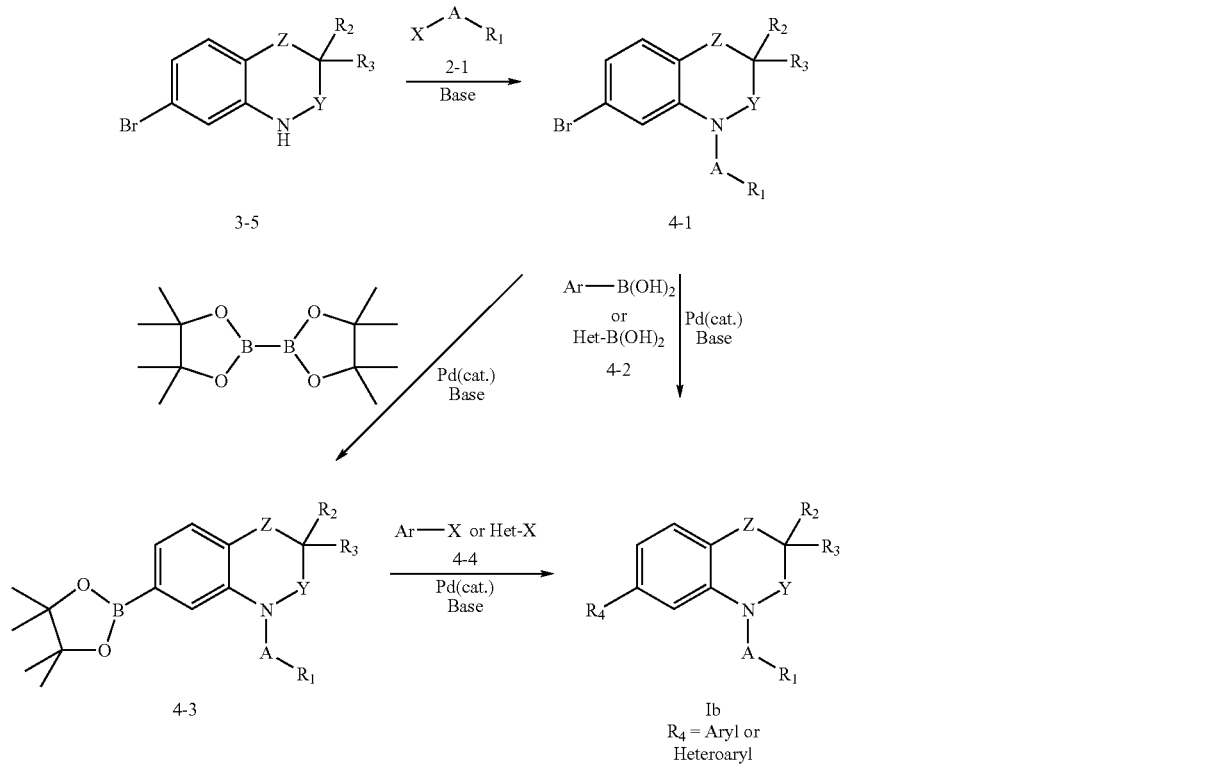

Intermediate 3-5 can be used to complete the synthesis of compound Ib as shown in Scheme 4.

Intermediate 3-5 is treated with an acid halide, acid anhydride or sulfonyl halide in dichloromethane in the presence of base (such as aqueous inorganic bicarbonate, or a tertiary amine base and/or DMAP). The resulting intermediate 4-1 is converted directly to compound Ib by treatment with an aryl or heteroaryl boronic acid in the presence of a palladium catalyst such as $PdCl_2(dppf)$ or $Pd(PPh_3)_4$ and a base such as potassium carbonate in a solvent such as DMF or dioxane. Alternatively, intermediate 4-1 can be converted to a boronate ester such as 4-3 by conditions well-known in the art, such as with (bis(pinacolato)diboron, potassium acetate and $PdCl_2$(dppf)). Treatment of 4-3 with an aryl or heteroaryl halide such as 4-4 in the presence of an appropriate palladium catalyst such as $PdCl_2(dppf)$ or $Pd(PPh_3)_4$ and a base such as potassium carbonate in a solvent such as DMF or dioxane provides compounds of general formula Ib.

Scheme 5

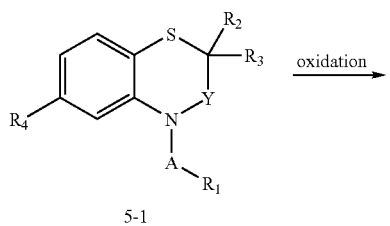

-continued

[structures Ic and Id]

The compound of formula 5-1 is an analog of Ia or Ib wherein the Z atom is sulfur. Compounds of formula Ic and Id can be prepared according to Scheme 5. Treatment of compounds of formula 5-1 with an oxidizing agent such as mCPBA in aprotic solvents (such as, for instance, DCM) provides the compounds of formula Ic and Id. Careful control of the oxidant stoichiometry will selectively provide compounds of formula Ic when one equivalent of oxidant is used, or compounds of formula Id when two or more equivalents of oxidant are used.

Intermediate 2-3 can be used to complete the synthesis of the compounds of formulas Ie, If, Ig and Ih as depicted in Scheme 6, below. For example, intermediate 2-3 can be coupled with nucleophiles 6-1, 6-2, 6-3 and 6-4 in a single step by traditional peptide coupling conditions (e.g. TBTU; or EDCI, HOBt). Alternatively, intermediate 2-3 can be coupled with nucleophiles 6-1, 6-2, 6-3 and 6-4 or through a two step procedure by first converting intermediate 2-3 to the acid chloride followed by coupling in DCM in the presence of an aqueous bicarbonate solution.

Cyclization of the coupled intermediates provides compounds of formulas Ie, If, Ig and Ih. For example, cyclization of the amide generated in Method 1 with an ammonia source provides compounds of formula Ie.

Similarly, cyclization of the amide generated in Method 2 under basic conditions in a polar aprotic solvent such as DMF provides the bicyclic oxazole compounds If.

Alternatively, coupled intermediates generated in Method 3 may be cyclized by treatment with TBAF in an ethereal solvent such as THF providing substituted 1,2,4-oxadiazolyl compounds having the structure of Ig.

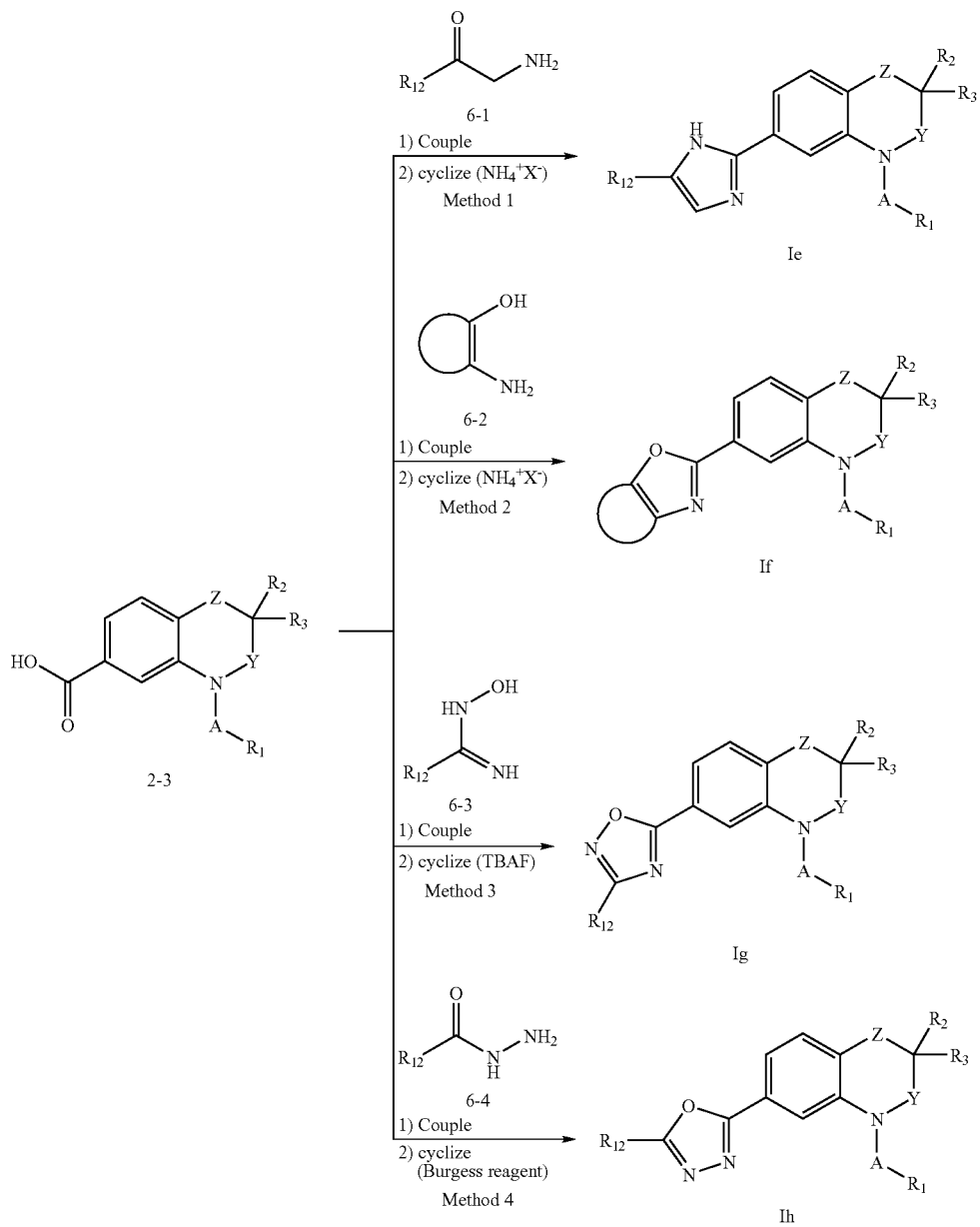

Furthermore, coupled intermediates generated in Method 4 may be cyclized by treatment with Burgess reagent in a polar aprotic solvent such as DMF at elevated temperatures, by, for instance, heating using microwave irradiation providing substituted 1,3,4-oxadiazolyl compounds having the structure of Ih.

EXAMPLES

Intermediate A: Preparation of N-isobutyl-3,4-dihydro-2H-benzo[b][1,4]thiazine-6-carboxamide

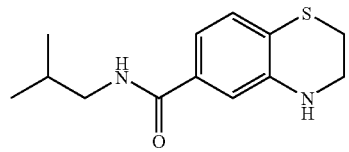

Step 1: Preparation of 4-(2-hydroxyethylthio)-3-nitrobenzoic acid

To a solution of 4-fluoro-3-nitrobenzoic acid (15 g, 81 mmol) in DMF (250 ml) was added 2-mercaptoethanol (6.27 ml, 89 mmol), and potassium carbonate (28.0 g, 203 mmol).

The reaction was allowed to stir over night. The reaction mixture had turned solid and yellow. TLC analysis indicated consumption of starting material. The reaction mixture was treated with H$_2$O (300 mL) and extracted with DCM (2×100 mL). The aqueous layer was then treated with concentrated HCl until a pH of 1 was attained. The organic layer was extracted with EtOAc (4×150 mL). The combined EtOAc extracts were dried over Na$_2$SO$_4$ and concentrated in vacuo to provide 4-(2-hydroxyethylthio)-3-nitrobenzoic acid (19.24 g, 79. mmol) in 98% yield, which was used without further purification.

Step 2: Preparation of
4-(2-chloroethylthio)-3-nitrobenzoyl chloride

To a suspension of 4-(2-hydroxyethylthio)-3-nitrobenzoic acid (8 g, 32.9 mmol) in toluene (250 ml) was added thionyl chloride (9.60 ml, 132 mmol). The reaction was heated to 80° C. and stirred for 3 hours. The reaction was cooled to room temperature and the clear solution was concentrated in vacuo. The residue was dissolved with DCM and concentrated in vacuo (2×) to provide the desired 4-(2-chloroethylthio)-3-nitrobenzoyl chloride as a yellow solid, which was used without further purification. Product yield was assumed to be 100% (9.21 g, 32.9 mmol) for future calculations.

Step 3: Preparation of
4-(2-chloroethylthio)-N-isobutyl-3-nitrobenzamide

To a biphasic solution of 4-(2-chloroethylthio)-3-nitrobenzoyl chloride (2.331 g, 8.32 mmol) in dichloromethane (75 mL) and saturated aqueous NaHCO$_3$ (75 mL) was added isobutylamine (1.043 mL, 10.40 mmol). The reaction was allowed to stir for 16 hours. TLC and LCMS analysis of the reaction mixture indicated consumption of starting material. The reaction mixture was diluted with H$_2$O (100 mL) and extracted with DCM (4×50 mL). The combined organics were dried over Na$_2$SO$_4$ and concentrated in vacuo. The product, 4-(2-chloroethylthio)-N-isobutyl-3-nitrobenzamide, was used without further purification. Product yield was assumed to be 100% (2.64 g, 8.32 mmol) for future calculations. LCMS (+ESI) m/z=317.13 [M+H]$^+$.

Step 4: Preparation of
3-amino-4-(2-chloroethylthio)-N-isobutylbenzamide

To a solution of 4-(2-chloroethylthio)-N-isobutyl-3-nitrobenzamide (2.38 g, 8.32 mmol) in AcOH (100 mL) was added iron (1.859 g, 33.3 mmol). The mixture was heated to 70° C. and the reaction was allowed to stir for 1 hour. The reaction turned from a dark solution to a light grey slurry. LCMS analysis of the reaction mixture indicated consumption of starting material. The reaction mixture was concentrated in vacuo and the resulting solid was diluted with H$_2$O (250 mL). The pH of the solution was adjusted to 6 by addition of solid K$_3$PO$_4$. The resulting slurry was extracted with EtOAc (4×100 mL). The combined organics were washed with saturated aqueous NaHCO$_3$ (50 mL) and brine (50 mL). The combined organics were then dried over Na$_2$SO$_4$ and concentrated in vacuo. The product, 3-amino-4-(2-chloroethylthio)-N-isobutylbenzamide, was used without further purification. Product yield was assumed to be 100% (2.38 g, 8.32 mmol) for future calculations. LCMS (+ESI) m/z=287.11 [M+H]$^+$.

Step 5: Preparation of N-isobutyl-3,4-dihydro-2H-benzo[b][1,4]thiazine-6-carboxamide To a solution of 3-amino-4-(2-chloroethylthio)-N-isobutylbenzamide (2.386 g, 8.32 mmol) in 2-butanone (150 ml) was added sodium iodide (1.247 g, 8.32 mmol). The reaction was heated to 70° C. and stirred for 24 hours. TLC analysis of the reaction mixture indicated consumption of starting material. The reaction mixture was concentrated in vacuo and purified by flash column chromatography [gradient elution (hexanes with 5-50% EtOAc)] to provide N-isobutyl-3,4-dihydro-2H-benzo[b][1,4]-thiazine-6-carboxamide (1.61 g, 6.43 mmol) as an off white solid. The total overall yield for steps 2-5 was 77%. LCMS (+ESI) m/z=523.34 [2M+Na]$^+$.

The compounds listed in Table 1 were prepared using the procedure described for the synthesis of Intermediate A. These compounds were prepared by treating 4-(2-chloroethylthio)-3-nitrobenzoyl chloride under the above-described conditions, with the appropriate amine. For example, Intermediate B, C, and D were prepared by substituting tert-butylamine, cyclopentylamine, and 3-methoxypropylamine respectively in place of isobutylamine in step 3 of the preparation of Intermediate A.

TABLE 1

| Intermediate | Compound | Name | LCMS |
|---|---|---|---|
| B | | N-tert-butyl-3,4-dihydro-2H-benzo[b][1,4]thiazine-6-carboxamide | [M + H]$^+$ = 251.12 |
| C | | N-cyclopentyl-3,4-dihydro-2H-benzo[b][1,4]thiazine--6-carboxamide | [M + H]$^+$ = 263.18 |
| D | | N-(3-methoxypropyl)-3,4-dihydro-2H-benzo[b][1,4]thiazine-6-carboxamide | [M + H]$^+$ = 267.23 |

TABLE 1-continued

| Intermediate | Compound | Name | LCMS |
|---|---|---|---|
| E | 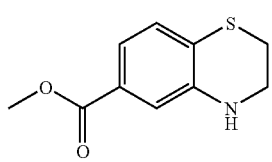 | N-(1-adamanyl)-3,4-dihydro-2H-benzo[b][1,4]thiazine-6-carboxamide | $[M + H]^+ =$ 329.27 |
| F | 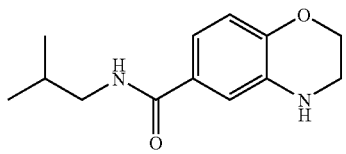 | N-isopropyl-3,4-dihydro-2H-benzo[b][1,4]thiazine-6-carboxamide | $[M + H]^+ =$ 237.09 |

Intermediate G: Preparation of methyl 3,4-dihydro-2H-benzo[b][1,4]thiazine-6-carboxylate

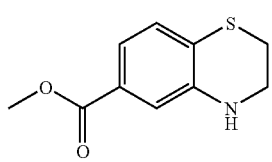

Step 1: Preparation of methyl 4-(2-chloroethylthio)-3-nitrobenzoate

To a solution of 4-(2-chloroethylthio)-3-nitrobenzoyl chloride (22 mg, 0.080 mmol) in MeOH (5 mL) was added triethylamine (0.112 mL, 0.800 mmol). The reaction mixture was allowed to stir for 1 h. TLC analysis of the reaction mixture indicated consumption of starting material. The reaction was concentrated under reduced pressure to provide methyl 4-(2-chloroethylthio)-3-nitrobenzoate (22 mg, 0.080 mmol) as a crude semi-solid, which was used without further purification.

Step 2: Preparation of methyl 3-amino-4-(2-chloroethylthio)benzoate

To a solution of 4-(2-chloroethylthio)-3-nitrobenzoate (22 mg, 0.080 mmol) in AcOH (4 mL) was added iron (18 mg, 0.322 mmol). The reaction mixture was heated to 70° C. and stirred for 1 hour. The reaction was cooled to room temperature and TLC analysis of the reaction mixture indicated that starting material had been consumed. The reaction mixture was concentrated in vacuo. The resulting paste was diluted with H$_2$O (10 mL) and treated with solid K$_3$PO$_4$ until a pH of 6 was achieved. The aqueous phase was extracted with EtOAC (3×10 mL). The combined organics were dried over anhydrous Na$_2$SO$_4$ and concentrated in vacuo. The resulting solid, methyl 3-amino-4-(2-chloroethylthio)benzoate (19.7 mg, 0.080 mmol), was used without further purification.

Step 3: Preparation of methyl 3,4-dihydro-2H-benzo[b][1,4]thiazine-6-carboxylate To a solution of methyl 3-amino-4-(2-chloroethylthio)benzoate (19.7 mg, 0.080 mmol) in 2-butanone (2 mL) was added sodium iodide (36 mg, 0.240 mmol). The reaction mixture was heated to 70° C. and stirred over night at that temperature. The reaction mixture was cooled to room temperature. TLC and LCMS analysis of the reaction mixture indicated product formation. The product was purified by flash column chromatography [gradient elution with Hexanes and 5-50% EtOAc]. To provide methyl 3,4-dihydro-2H-benzo[b][1,4]thiazine-6-carboxylate (8.6 mg, 0.040 mmol, 49.6% overall 3 steps) as an off-white solid.

Intermediate H: Preparation of N-isobutyl-3,4-dihydro-2H-benzo[b][1,4]oxazine-6-carboxamide

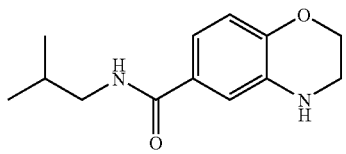

This compound was prepared using the procedure outlined in the synthesis of Intermediate A, with substitution of ethylene glycol for 2-mercaptoethanol in step 1. N-isobutyl-3,4-dihydro-2H-benzo[b][1,4]oxazine-6-carboxamide (100.3 mg, 0.428 mmol) was isolated as a white solid in 20% overall yield. LCMS (+ESI) m/z=235.05 [M+H]$^+$.

Intermediate I: Preparation of N-cyclopentyl-3,4-dihydro-2H-benzo[b][1,4]oxazine-6-carboxamide

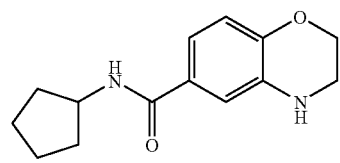

This compound was prepared using the procedure outlined in the synthesis of Intermediate A, with substitution of ethylene glycol for 2-mercaptoethanol in step 1 and cyclopentylamine for isobutylamine in step 3. N-cyclopentyl-3,4-dihydro-2H-benzo[b][1,4]oxazine-6-carboxamide (106.2 mg, 0.431 mmol) was isolated as a white solid in 22% overall yield. LCMS (+ESI) m/z=247.07 [M+H]+.

Intermediate J: Preparation of 4-(4-fluorophenylsulfonyl)-3,4-dihydro-2H-benzo[b][1,4]thiazine-6-carboxylic acid

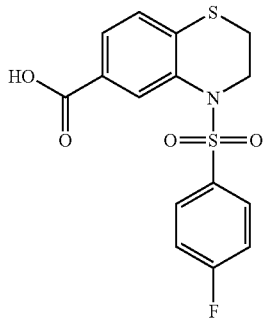

Step 1: Preparation of methyl 4-(4-fluorophenylsulfonyl)-3,4-dihydro-2H-benzo[b][1,4]thiazine-6-carboxylate To a solution of Intermediate G (1.2455 g, 5.95 mmol) in DCE (3 ml) was added 4-fluorobenzenesulfonyl chloride (0.930 g, 4.78 mmol) and DIPEA (1.1 ml, 6.30 mmol). The reaction vial was capped and subjected to microwave irradiation (100° C., 5 min). Analysis of the reaction mixture indicated partial consumption of starting material. The reaction mixture was resubjected to microwave irradiation (120° C., 5 minutes). The reaction mixture was washed with H$_2$O and the aqueous layer was extracted twice with DCM. The combined organics were dried over anhydrous Na$_2$SO$_4$, filtered and concentrated in vacuo to provide a crude mixture of methyl 4-(4-fluorophenylsulfonyl)-3,4-dihydro-2H-benzo[b][1,4]thiazine-6-carboxylate as a brown oil (1.779 g, 4.84 mmol, 81% yield). This material was used without purification. LCMS (+ESI) m/z=368.0 [M+H]$^+$.

Step 2: Preparation of 4-(4-fluorophenylsulfonyl)-3,4-dihydro-2H-benzo[b][1,4]thiazine-6-carboxylic acid To a solution of methyl 4-(4-fluorophenylsulfonyl)-3,4-dihydro-2H-benzo[b][1,4]thiazine-6-carboxylate (1.779 g, 4.84 mmol) in THF (12 mL) and water (6 mL) was added LiOH (0.6096 g). The reaction was allowed to stir at room temperature for 16 hours. LCMS analysis identified the product as the predominant component of the reaction mixture. The solvent was removed under reduced pressure. The resulting aqueous solution was acidified with 1N HCl to provide a white precipitate. The aqueous layer was extracted with DCM until the acid was no longer detected in the organic wash layer. The combined organics were washed with H$_2$O and dried over anhydrous Na$_2$SO$_4$, filtered and concentrated in vacuo. The mixture was purified by flash chromatography using a gradient elution of hexane with 0-95% ethyl acetate doped with 1% AcOH. The product, 4-(4-fluorophenylsulfonyl)-3,4-dihydro-2H-benzo[b][1,4]thiazine-6-carboxylic acid (1.108 g, 3.14 mmol, 65% yield), was isolated as off-white solid. LCMS (+ESI) m/z=354.0 [M+H]$^+$.

The compounds listed in Table 2 were prepared using the procedure described for the synthesis of Intermediate J. These compounds were prepared by treating methyl 3,4-dihydro-2H-benzo[b][1,4]thiazine-6-carboxylate under the above-described conditions, with the appropriate sulfonyl chloride. For example, Intermediate K, L, and M were prepared by substituting benzenesulfonyl chloride, 4-(trifluoromethyl) benzenesulfonyl chloride, and 1-methyl-1H-imidazolesulfonyl chloride respectively in place of 4-fluorobenzenesulfonyl chloride in step 1 of the preparation of Intermediate J.

TABLE 2

| Intermediate | Compound | Name | LCMS |
|---|---|---|---|
| K | | 4-(phenylsulfonyl)-3,4-dihydro-2H-benzo[b][1,4]thiazine-6-carboxylic acid | [M + H]$^+$ = 336.0 |
| L | | 4-(4-(trifluoromethyl)phenylsulfonyl)-3,4-dihydro-2H-benzo[b][1,4]thiazine-6-carboxylic acid | [M + H]$^+$ = 404.0 |

TABLE 2-continued

| Intermediate | Compound | Name | LCMS |
|---|---|---|---|
| M | | 4-(1-methyl-1H-imidazol-4-ylsulfonyl)-3,4-dihydro-2H-benzo[b][1,4]thiazine-6-carboxylic acid | [M + H]⁺ = 339.8 |

Intermediate N: Preparation of methyl 2,2-dimethyl-2,3,4,5-tetrahydrobenzo[b][1,4]-thiazepine-7-carboxylate

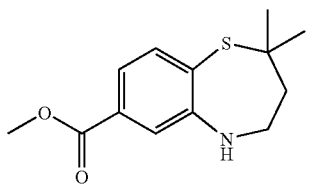

Step 1: Preparation of 4-(4-hydroxy-2-methylbutan-2-ylthio)-3-nitrobenzoic acid To a solution of 4-fluoro-3-nitrobenzoic acid (2 g, 10.80 mmol) in DMF (50 ml) was added potassium carbonate (3.73 g, 27.0 mmol), and 3-mercapto-3-methylbutan-1-ol (1.450 ml, 11.88 mmol). The reaction was stirred at room temperature for 16 hours. The reaction mixture had turned yellow overnight. The DMF was removed under reduced pressure and the resulting slurry was diluted with EtOAc (100 mL) and extracted with $H_2O$ (100 mL). The aqueous layer was then treated with conc. HCl until a precipitate formed. The mixture was extracted with EtOAc (3×100 mL) and the combined organics were dried over $Na_2SO_4$ and concentrated in vacuo. The product was isolated as a yellow solid and used without further purification.

Step 2: Preparation 4-(4-chloro-2-methylbutan-2-ylthio)-3-nitrobenzoyl chloride To a solution of 4-(4-hydroxy-2-methylbutan-2-ylthio)-3-nitrobenzoic acid (3.08 g, 10.8 mmol) in DCE (50 mL) was added thionyl chloride (2.365 mL, 32.4 mmol). The reaction was heated to 70° C. and stirred at that temperature for 1 hour. The solvent was removed under reduced pressure and the resulting oil was used without further purification.

Step 3: Preparation of methyl 4-(4-chloro-2-methylbutan-2-ylthio)-3-nitrobenzoate To a solution of 4-(4-chloro-2-methylbutan-2-ylthio)-3-nitrobenzoyl chloride (3.48 g, 10.8 mmol) in MeOH (200 mL) was added triethylamine (15.05 mL, 108 mmol). The reaction was stirred at room temperature for 3 hours. The solvent was removed under reduced pressure. The resulting paste was diluted with EtOAc (200 mL) and washed with saturated aqueous $NaHCO_3$ (75 mL). The organic layer was dried over $Na_2SO_4$ and concentrated in vacuo. The resulting solid was used without further purification.

Step 4: Preparation of methyl 3-amino-4-(4-chloro-2-methylbutan-2-ylthio)benzoate To a solution of methyl 4-(4-chloro-2-methylbutan-2-ylthio)-3-nitrobenzoate (3.43 g, 10.8 mmol) in AcOH (100 mL) was added iron (2.413 g, 43.2 mmol). The reaction was heated to 70° C. and stirred at that temperature for 2 hours. The solvent was removed under reduced pressure and the resulting paste was diluted with H2O (250 mL). The solution was treated with $K_3PO_4$ until pH=6. The aqueous layer was extracted with EtOAc (3×150 mL). The combined organics were washed with saturated aqueous $NaHCO_3$ (50 mL) and brine (50 mL) then dried over $Na_2SO_4$ and concentrated in vacuo. The product was isolated as a brown solid and used without further purification.

Step 5: Preparation of methyl 2,2-dimethyl-2,3,4,5-tetrahydrobenzo[b][1,4]thiazepine-7-carboxylate To a solution of methyl 3-amino-4-(4-chloro-2-methylbutan-2-ylthio)benzoate (3.11 g, 10.8 mmol) in 2-butanone (150 mL) was added sodium iodide (4.86 g, 32.4 mmol). The reaction was heated to 70° C. and stirred at that temperature for 16 hours. Thin layer chromatography and LCMS analysis of the reaction mixture indicated consumption of starting material. The solvent was removed under reduced pressure and the resulting red slurry was diluted with EtOAc (200 mL). The organic layer was washed with saturated aqueous $NaHCO_3$ (100 mL) and aqueous sodium hydrosulifte (50 mL). The organic layer was dried over $Na_2SO_4$ and concentrated in vacuo. The resulting solid was purified by flash column chromatography using a gradient elution of hexanes with 5-70% EtOAc to provide methyl 2,2-dimethyl-2,3,4,5-tetrahydrobenzo-[b][1,4]thiazepine-7-carboxylate (1.82 g, 7.24 mmol, 67.0% yield) as an off white solid. LCMS (+ESI) m/z=252.1 [M+H]⁺; ¹H-NMR ($CDCl_3$) δ 7.48-7.40 (m, 3H), 4.25-4.06 (br s, 1H), 3.88 (s, 3H), 3.25 (m, 2H), 2.00 (m, 2H), 1.33 (s, 6H).

Intermediate O: Preparation of 2,2-dimethyl-5-(phenylsulfonyl)-2,3,4,5-tetrahydrobenzo-[b][1,4]thiazepine-7-carboxylic acid

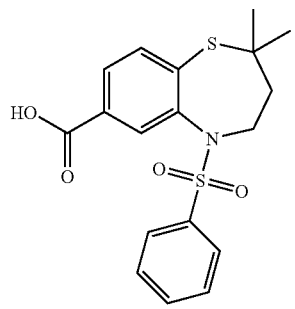

Step 1: Preparation of methyl 2,2-dimethyl-5-(phenylsulfonyl)-2,3,4,5-tetrahydrobenzo-[b][1,4]thiazepine-7-carboxylate To a solution of Intermediate N (400 mg, 1.591 mmol) in DCM (20 mL) was added benzenesulfonyl chloride (0.408 mL, 3.18 mmol), DIPEA (1.112 mL, 6.37 mmol) and DMAP (97 mg, 0.796 mmol). The reaction was stirred at room temperature for 16 hours. TLC analysis of the reaction mixture indicated consumption of starting material. The reaction mixture was washed with saturated aqueous $NaHCO_3$ (20 mL) and the aqueous layer was back extracted with DCM (20 mL). The combined organics were dried over Na2SO4 and concentrated in vacuo. The resulting solid was purified by flash column chromatography using a gradient elution of hexanes with 5-70% EtOAc to provide methyl 2,2-dimethyl-5-(phenylsulfonyl)-2,3,4,5-tetrahydrobenzo[b][1,4]thiazepine-7-carboxylate (502 mg, 1.282 mmol, 81% yield) as a tan solid. LCMS (+ESI) m/z=391.9 [M+H]$^+$.

Step 2: Preparation of 2,2-dimethyl-5-(phenylsulfonyl)-2,3,4,5-tetrahydrobenzo[b][1,4]-thiazepine-7-carboxylic acid To a solution of methyl 2,2-dimethyl-5-(phenylsulfonyl)-2,3,4,5-tetrahydrobenzo[b][1,4]thiazepine-7-carboxylate (450 mg, 1.149 mmol) in THF (10 mL), MeOH (10.00 mL) and water (10.00 mL) was added lithium hydroxide (55.1 mg, 2.299 mmol). The reaction was allowed to stir at room temperature for 8 h. The solvent was removed under reduced pressure. The aqueous solution was acidified with 1 N HCl (10 mL), which resulted in the formation of a white solid. The mixture was washed with EtOAc (3×30 mL) and the combined organics were dried over $Na_2SO_4$ and concentrated in vacuo. 2,2-dimethyl-5-(phenylsulfonyl)-2,3,4,5-tetrahydrobenzo[b][1,4]thiazepine-7-carboxylic acid (434 mg, 1.149 mmol, 100% yield) was isolated as an off white solid and used without further purification. LCMS (+ESI) m/z=377.9 [M+H]$^+$.

Intermediate P: Preparation of 5-(4-fluorophenylsulfonyl)-2,2-dimethyl-2,3,4,5-tetrahydrobenzo[b][1,4]thiazepine-7-carboxylic acid

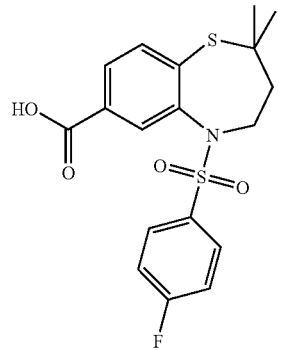

This compound was prepared using the procedure outlined in the synthesis of Intermediate O, with substitution of 4-fluorobenzenesulfonyl chloride for benzenesulfonyl chloride in step 1. LCMS (+ESI) m/z=395.9 [M+H]$^+$.

Example 1

Preparation of 4-(4-chlorobenzoyl)-N-isobutyl-3,4-dihydro-2H-benzo[b][1,4]thiazine-6-carboxamide

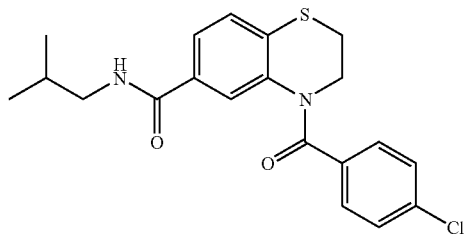

To a biphasic mixture of Intermediate A (15.6 mg, 0.062 mmol) in dichloromethane (2 mL) and saturated aqueous $NaHCO_3$ (2 mL) was added 4-chlorobenzoyl chloride (25 μL, 0.195 mmol). The reaction was allowed to stir for 16 hours. TLC analysis of the reaction mixture indicated consumption of starting material. The reaction mixture was extracted with DCM (3×2 mL). The combined organics were dried over $Na_2SO_4$ and concentrated under a stream of nitrogen. The mixture was purified by flash column chromatography [gradient elution (hexanes with 5-50% EtOAc)] to provide the compound 4-(4-chlorobenzoyl)-N-isobutyl-3,4-dihydro-2H-benzo[b][1,4]thiazine-6-carboxamide (19.1 mg, 0.049 mmol) in 79% yield as an off white solid. LCMS (+ESI) m/z=389.2 [M+H]$^+$; $^1$H-NMR ($CD_2Cl_2$) δ 7.30 (dd, 1H), 7.20 (d, 1H), 7.19 (s, 4H), 6.83 (br s, 1H), 5.53 (br s, 1H), 4.08 (m, 2H), 3.25 (m, 2H), 3.00 (m, 2H), 1.65 (m, 1H), 0.78 (d, 6H).

The compounds listed in Table 3 were prepared using the procedure described for the synthesis of the compound of Example 1. These compounds can be prepared using the appropriate intermediate chosen from Intermediates A-F, and treating that intermediate under the above-described conditions, with the appropriate substituted or unsubstituted benzoyl chloride as detailed above.

TABLE 3

| Example | Compound | Name | MS |
|---|---|---|---|
| 2 | | 4-benzoyl-N-isobutyl-3,4-dihydro-2H-benzo[b][1,4]thiazine-6-carboxamide | [M + H]$^+$ = 355.3 |
| 3 | | 4-(4-fluorobenzoyl)-N-isobutyl-3,4-dihydro-2H-benzo[b][1,4]thiazine-6-carboxamide | [M + H]$^+$ = 372.1 |
| 4 | | Preparation of N-isobutyl-4-(4-methyl benzoyl)-3,4-dihydro-2H-benzo[b][1,4]thiazine-6-carboxamide | [M + H]$^+$ = 369.3 |
| 5 | | N-isobutyl-4-(4-methoxybenzoyl)-3,4-dihydro-2H-benzo[b][1,4]thiazine-6-carboxamide | [M + H]$^+$ = 385.3 |
| 6 | | Preparation of N-tert-butyl-4-(4-fluoro benzoyl)-3,4-dihydro-2H-benzo[b][1,4]thiazine-6-carboxamide | [M + H]$^+$ = 373.2 |
| 7 | | N-tert-butyl-4-(4-methoxybenzoyl)-3,4-dihydro-2H-benzo[b][1,4]thiazine-6-carboxamide | [M + H]$^+$ = 385.2 |

TABLE 3-continued

| Example | Compound | Name | MS |
|---|---|---|---|
| 8 | | N-tert-butyl-4-(4-methylbenzoyl)-3,4-dihydro-2H-benzo[b][1,4]thiazine-6-carboxamide | [M + H]$^+$ = 369.3 |
| 9 | | 4-benzoyl-N-tert-butyl-3,4-dihydro-2H-benzo[b][1,4]thiazine-6-carboxamide | [M + H]$^+$ = 355.2 |
| 10 | | N-tert-butyl-4-(4-chlorobenzoyl)-3,4-dihydro-2H-benzo[b][1,4]thiazine-6-carboxamide | [M + H]$^+$ = 389.2 |
| 11 | | N-cyclopentyl-4-(4-methoxybenzoyl)-3,4-dihydro-2H-benzo[b][1,4]thiazine-6-carboxamide | [M + H]$^+$ = 397.3 |
| 12 | | N-cyclopentyl-4-(4-fluorobenzoyl)-3,4-dihydro-2H-benzo[b][1,4]thiazine-6-carboxamide | [M + H]$^+$ = 385.3 |
| 13 | | N-cyclopentyl-4-(4-methylbenzoyl)-3,4-dihydro-2H-benzo[b][1,4]thiazine-6-carboxamide | [M + H]$^+$ = 381.3 |

TABLE 3-continued

| Example | Compound | Name | MS |
|---|---|---|---|
| 14 | | 4-benzoyl-N-cyclopentyl-3,4-dihydro-2H-benzo[b][1,4]thiazine-6-carboxamide | [M + H]⁺ = 367.2 |
| 15 | | N-cyclopentyl-4-(4-chlorobenzoyl)-3,4-dihydro-2H-benzo[b][1,4]thiazine-6-carboxamide | [M + H]⁺ = 401.2 |
| 16 | | 4-benzoyl-N-(3-methoxypropyl)-3,4-dihydro-2H-benzo[b][1,4]thiazine-6-carboxamide | [M + H]⁺ = 371.2 |
| 17 | | 4-(4-fluorobenzoyl-N-(3-methoxypropyl)-3,4-dihydro-2H-benzo[b][1,4]thiazine-6-carboxamide | [M + H]⁺ = 389.3 |
| 18 | | N-(3-methoxypropyl)-4-(4-methylbenzoyl)-3,4-dihydro-2H-benzo[b][1,4]thiazine-6-carboxamide | [M + H]⁺ = 385.3 |
| 19 | | 4-(4-chlorobenzoyl-N-(3-methoxypropyl)-3,4-dihydro-2H-benzo[b][1,4]thiazine-6-carboxamide | [M + H]⁺ = 405.2 |

TABLE 3-continued

| Example | Compound | Name | MS |
|---------|----------|------|-----|
| 20 | | 4-(4-methoxybenzoyl-N-(3-methoxypropyl)-3,4-dihydro-2H-benzo[b][1,4]thiazine-6-carboxamide | [M + H]+ = 401.2 |
| 21 | | 4-benzoyl-N-(1-adamantyl)-3,4-dihydro-2H-benzo[b][1,4]thiazine-6-carboxamide | [M + H]+ = 433.3 |
| 22 | | 4-(4-fluorobenzoyl-N-(1-adamantyl)-3,4-dihydro-2H-benzo[b][1,4]thiazine-6-carboxamide | [M + H]+ = 451.3 |
| 23 | | N-(1-adamantyl)-4-(4-methylbenzoyl)-3,4-dihydro-2H-benzo[b][1,4]thiazine-6-carboxamide | [M + H]+ = 447.3 |
| 24 | | N-(1-adamantyl)-4-(4-chlorobenzoyl)-3,4-dihydro-2H-benzo[b][1,4]thiazine-6-carboxamide | [M + H]+ = 467.3 |
| 25 | | N-(1-adamantyl)-4-(4-methoxybenzoyl)-3,4-dihydro-2H-benzo[b][1,4]thiazine-6-carboxamide | [M + H]+ = 463.4 |

TABLE 3-continued

| Example | Compound | Name | MS |
|---|---|---|---|
| 26 | | 4-benzoyl-N-isopropyl-3,4-dihydro-2H-benzo[b][1,4]thiazine-6-carboxamide | [M + H]+ = 341.2 |
| 27 | | 4-(4-fluorobenzoyl-N-isopropyl-3,4-dihydro-2H-benzo[b][1,4]thiazine-6-carboxamide | [M + H]+ = 359.2 |
| 28 | | N-isopropyl-4-(4-methylbenzoyl)-3,4-dihydro-2H-benzo[b][1,4]thiazine-6-carboxamide | [M + H]+ = 355.2 |
| 29 | | 4-(4-chlorobenzoyl-N-isopropyl-3,4-dihydro-2H-benzo[b][1,4]thiazine-6-carboxamide | [M + H]+ = 375.2 |
| 30 | | N-isopropyl-4-(4-methoxybenzoyl)-3,4-dihydro-2H-benzo[b][1,4]thiazine-6-carboxamide | [M + H]+ = 371.2 |

Example 31

Preparation of 4-isobutyryl-N-isopropyl-3,4-dihydro-2H-benzo[b][1,4]thiazine-6-carboxamide

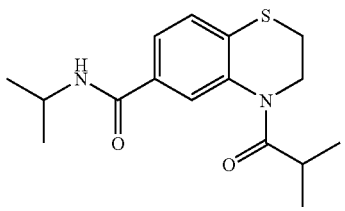

To a biphasic mixture of Intermediate F (20.3 mg, 0.086 mmol) in dichloromethane (2 mL) and saturated aqueous NaHCO$_3$ (2 mL) was added isobutyryl chloride (50 µl, 0.477 mmol). The reaction was allowed to stir for 16 hours. TLC analysis of the reaction mixture indicated consumption of starting material. The reaction mixture was extracted with DCM (3×2 mL). The combined organics were dried over Na$_2$SO$_4$ and concentrated under a stream of nitrogen. The mixture was purified by flash column chromatography [gradient elution (hexanes with 5-60% EtOAc)] to provide 4-isobutyryl-N-isopropyl-3,4-dihydro-2H-benzo[b][1,4]thiazine-6-carboxamide (9.1 mg, 0.030 mmol) in 34% yield as an off white solid. LCMS (+ESI) m/z=307.23 [M+H]$^+$; $^1$H-NMR (CD$_2$Cl$_2$) δ 7.62 (br s, 1H), 7.42 (dd, 1H), 7.28 (d, 1H), 5.93 (br s, 1H), 4.19 (m, 1H), 3.93 (br s, 1H), 3.22 (m, 2H), 3.01 (m, 1H), 1.24 (d, 6H), 1.23 (m, 1H), 1.04 (d, 6H).

The compounds listed in Table 4 were prepared using the procedure outlined in the synthesis of the compound of Example 31. These compounds can be prepared using the appropriate intermediate (selected from Intermediates B to E) and treating that intermediate, under the above-described conditions, with the appropriate alkyl chloride.

TABLE 4

| Example | Compound | Name | MS |
|---|---|---|---|
| 32 | | 4-acetyl-N-tert-butyl-3,4-dihydro-2H-benzo[b][1,4]thiazine-6-carboxamide | [M + H]$^+$ = 293.2 |
| 33 | | N-tert-butyl-4-propionyl-3,4-dihydro-2H-benzo[b][1,4]thiazine-6-carboxamide | [M + Na]$^+$ = 329.2 |
| 34 | | N-tert-butyl-4-isobutyryl-3,4-dihydro-2H-benzo[b][1,4]thiazine-6-carboxamide | [M + H]$^+$ = 321.2 |
| 35 | | 4-acetyl-N-cyclopentyl-3,4-dihydro-2H-benzo[b][1,4]thiazine-6-carboxamide | [M + H]$^+$ = 305.2 |
| 36 | | N-cyclopentyl-4-propionyl-3,4-dihydro-2H-benzo[b][1,4]thiazine-6-carboxamide | [M + H]$^+$ = 319.2 |

TABLE 4-continued

| Example | Compound | Name | MS |
|---|---|---|---|
| 37 | | N-cyclopentyl-4-isobutyryl-3,4-dihydro-2H-benzo[b][1,4]thiazine-6-carboxamide | [M + H]$^+$ = 333.2 |
| 38 | | 4-isobutyryl-N-(3-methoxypropyl)-3,4-dihydro-2H-benzo[b][1,4]thiazine-6-carboxamide | [M + H]$^+$ = 337.3 |
| 39 | | N-(1-adamantyl)-4-propionyl-3,4-dihydro-2H-benzo[b][1,4]thiazine-6-carboxamide | [M + H]$^+$ = 385.3 |
| 40 | | N-(1-adamantyl)-4-isobutyryl-3,4-dihydro-2H-benzo[b][1,4]thiazine-6-carboxamide | [M + H]$^+$ = 399.4 |

Example 41

Preparation of N-isobutyl-4-(phenylsulfonyl)-3,4-dihydro-2H-benzo-[b][1,4]thiazine-6-carboxamide

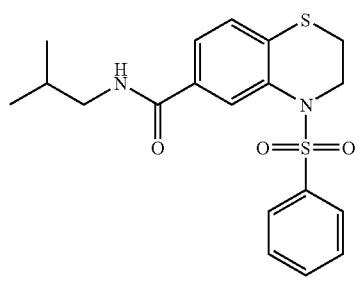

To a solution of Intermediate A (25 mg, 0.100 mmol) in dichloromethane (2 mL) was added benzenesulfonyl chloride (50 µL, 0.388 mmol), DIPEA (100 µL, 0.574 mmol) and DMAP (6.10 mg, 0.050 mmol). The reaction was allowed to continue with stirring for 72 hours. TLC analysis of the reaction mixture indicated consumption of starting material. The reaction mixture was concentrated under a stream of nitrogen and purified immediately. The mixture was purified by flash column chromatography [gradient elution (hexanes with 5-50% EtOAc)] to provide the desired compound: N-isobutyl-4-(phenylsulfonyl)-3,4-dihydro-2H-benzo[b][1,4]thiazine-6-carboxamide (31.5 mg, 0.081 mmol) in 81% yield as an off white solid. LCMS (+ESI) m/z=391.16 [M+H]$^+$; $^1$H-NMR (CD$_2$Cl$_2$) δ 7.96 (d, 1H), 7.61-7.55 (m, 3H), 7.53 (dd, 1H), 7.48-7.46 (m, 2H), 7.14 (d, 1H), 6.23 (br s, 1H), 3.98 (m, 2H), 3.25 (m, 2H), 2.87 (m, 2H), 1.89 (m, 1H), 0.97 (d, 6H).

Example 42

Preparation of (4-(4-fluorophenylsulfonyl)-3,4-dihydro-2H-benzo[b][1,4]thiazin-6-yl)(morpholino)methanone

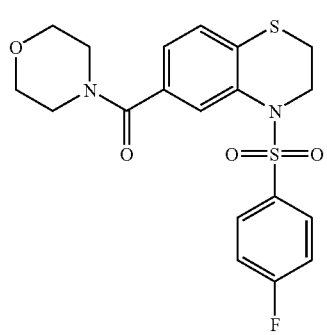

Step 1: Preparation of 4-(4-fluorophenylsulfonyl)-3,4-dihydro-2H-benzo[b][1,4]thiazine-6-carbonyl chloride To a suspension of Intermediate J (51.3 mg, 0.145 mmol) in DCM (1.5 mL) was added oxalyl chloride (316.58 µL, 3.62 mmol) and DMF (15 µL, 0.194 mmol) giving rise to an evolution of gas and resulting in a brown solution. The reaction was stirred at room temperature for 16 h. LCMS analysis of the reaction mixture showed complete consumption of starting material. The reaction mixture was concentrated under reduced pressure and the crude solid was used without purification. The yield was assumed to be 100% for calculation purposes in future reactions.

Step 2: Preparation of (4-(4-fluorophenylsulfonyl)-3,4-dihydro-2H-benzo[b][1,4]thiazin-6-yl)(morpholino)methanone To a suspension of 4-(4-fluorophenylsulfonyl)-3,4-dihydro-2H-benzo[b][1,4]thiazine-6-carbonyl chloride (0.027 g, 72.6 µmol) in DCE (1 mL) was added morpholine (15.97 µL, 182 µmol) and pyridine (350 µL). The reaction was heated to 70° C. and stirred at that temperature for 16 hours. LCMS analysis of the reaction mixture indicated complete consumption of starting material. The resulting solid was purified by flash column chromatography using a gradient elution of hexanes with 0-60% EtOAc to provide (4-(4-fluorophenylsulfonyl)-3,4-dihydro-2H-benzo[b][1,4]thiazin-6-yl)(morpholino)methanone (21.8 mg, 49.3 µmol, 88% yield for 2 steps) as off-white solid. LCMS (+ESI) m/z=423.5 [M+H]⁻.

The compounds listed in Table 5 were prepared using the procedure outlined in the synthesis of the compounds of Examples 41 and 42. Examples 43-57 can be prepared from the appropriate intermediate (selected from Intermediates A to F) by treatment with the appropriate sulfonyl chloride under the described conditions of Example 41. Examples 58-63 can be prepared from the appropriate intermediate (selected from Intermediates H and I) by treatment with the appropriate sulfonyl chloride under the described conditions of Example 41. Examples 64-79 can be prepared from the appropriate intermediate (selected from Intermediates J to L) by treatment with the appropriate amine under the described conditions of Example 42.

TABLE 5

| Example | Compound | Name | MS |
|---|---|---|---|
| 43 | (structure) | 4-(4-fluorophenyl sulfonyl)-N-isobutyl-3,4-dihydro-2H-benzo[b][1,4]thiazine-6-carboxamide | [M + H]⁺ = 409.3 |
| 44 | (structure) | N-cyclopentyl-4-(phenylsulfonyl)-3,4-dihydro-2H-benzo[b][1,4]thiazine-6-carboxamide | [M + H]⁺ = 403.1 |
| 45 | (structure) | N-cyclopentyl-4-(4-fluorophenylsulfonyl)-3,4-dihydro-2H-benzo[b][1,4]thiazine-6-carboxamide | [M + H]⁺ = 421.3 |

TABLE 5-continued

| Example | Compound | Name | MS |
|---|---|---|---|
| 46 | | N-tert-butyl-4-(phenylsulfonyl)-3,4-dihydro-2H-benzo[b][1,4]thiazine-6-carboxamide | [M + H]+ = 391.3 |
| 47 | | N-tert-butyl-4-(4-fluorophenylsulfonyl)-3,4-dihydro-2H-benzo[b][1,4]thiazine-6-carboxamide | [M + H]+ = 409.3 |
| 48 | | N-(3-methoxypropyl)-4-(phenylsulfonyl)-3,4-dihydro-2H-benzo[b][1,4]thiazine-6-carboxamide | [M + H]+ = 407.2 |
| 49 | | 4-(4-fluorophenylsulfonyl)-N-(3-methoxypropyl)-3,4-dihydro-2H-benzo[b][1,4]thiazine-6-carboxamide | [M + H]+ = 425.2 |
| 50 | | N-(1-adamantyl)-4-(phenylsulfonyl)-3,4-dihydro-2H-benzo[b][1,4]thiazine-6-carboxamide | [M + H]+ = 469.3 |

TABLE 5-continued

| Example | Compound | Name | MS |
|---|---|---|---|
| 51 | | N-(1-adamantyl)-4-(4-fluorophenylsulfonyl)-3,4-dihydro-2H-benzo[b][1,4]thiazine-6-carboxamide | [M + H]$^+$ = 487.3 |
| 52 | | N-isopropyl-4-(phenylsulfonyl)-3,4-dihydro-2H-benzo[b][1,4]thiazine-6-carboxamide | [M + H]$^+$ = 377.2 |
| 53 | | N-tert-butyl-4-(methylsulfonyl)-3,4-dihydro-2H-benzo[b][1,4]thiazine-6-carboxamide | [M + H]$^+$ = 329.2 |
| 54 | | N-isobutyl-4-(methylsulfonyl)-3,4-dihydro-2H-benzo[b][1,4]thiazine-6-carboxamide | [M + H]$^+$ = 329.2 |
| 55 | | N-cyclopentyl-4-(methylsulfonyl)-3,4-dihydro-2H-benzo[b][1,4]thiazine-6-carboxamide | [M + H]$^+$ = 341.2 |
| 56 | | N-(3-methoxypropyl)-4-(methylsulfonyl)-3,4-dihydro-2H-benzo[b][1,4]thiazine-6-carboxamide | [M + H]$^+$ = 345.2 |
| 57 | | N-isopropyl-4-(methylsulfonyl)-3,4-dihydro-2H-benzo[b][1,4]thiazine-6-carboxamide | [M + H]$^+$ = 315.1 |

TABLE 5-continued

| Example | Compound | Name | MS |
|---------|----------|------|-----|
| 58 | | 4-(4-chlorophenylsulfonyl)-N-isobutyl-3,4-dihydro-2H-benzo[b][1,4]oxazine-6-carboxamide | [M + H]⁺ = 409.0 |
| 59 | | N-isobutyl-4-(phenylsulfonyl)-3,4-dihydro-2H-benzo[b][1,4]oxazine-6-carboxamide | [M + H]⁺ = 375.1 |
| 60 | | 4-(4-fluorophenylsulfonyl)-N-isobutyl-3,4-dihydro-2H-benzo[b][1,4]oxazine-6-carboxamide | [M + H]⁺ = 393.1 |
| 61 | | N-cyclopentyl-4-(phenylsulfonyl)-3,4-dihydro-2H-benzo[b][1,4]oxazine-6-carboxamide | [M + H]⁺ = 387.1 |
| 62 | | N-cyclopentyl-4-(4-fluorophenylsulfonyl)-3,4-dihydro-2H-benzo[b][1,4]oxazine-6-carboxamide | [M + H]⁺ = 405.3 |

Note: MS values use $[M + H]^+$ notation.

TABLE 5-continued

| Example | Compound | Name | MS |
|---|---|---|---|
| 63 | | 4-(4-chlorophenylsulfonyl)-N-cyclopentyl-3,4-dihydro-2H-benzo[b][1,4]oxazine-6-carboxamide | [M + H]+ = 421.0 |
| 64 | | N,N-dimethyl-4-(phenylsulfonyl)-3,4-dihydro-2H-benzo[b][1,4]thiazine-6-carboxamide | [M + H]+ = 363.1 |
| 65 | | N,N-diethyl-4-(phenylsulfonyl)-3,4-dihydro-2H-benzo[b][1,4]thiazine-6-carboxamide | [M + H]+ = 391.0 |
| 66 | | (4-(phenylsulfonyl)-3,4-dihydro-2H-benzo[b][1,4]thiazin-6-yl)(pyrrolidin-1-yl)methanone | [M + H]+ = 389.0 |
| 67 | | (4-(phenylsulfonyl)-3,4-dihydro-2H-benzo[b][1,4]thiazin-6-yl)(piperidin-1-yl)methanone | [M + H]+ = 403.1 |

TABLE 5-continued

| Example | Compound | Name | MS |
|---|---|---|---|
| 68 | 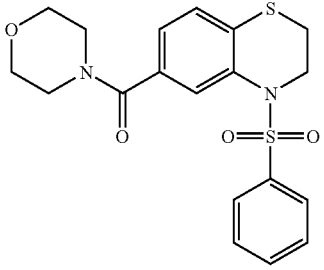 | morpholino(4-(phenylsulfonyl)-3,4-dihydro-2H-benzo[b][1,4]thiazin-6-carboxamide | [M + H]+ = 405.0 |
| 69 | 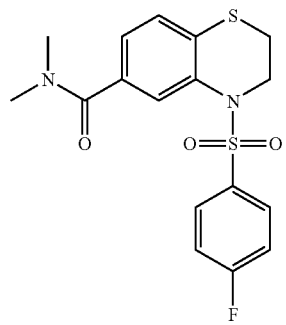 | 4-(4-fluorophenylsulfonyl)-N,N-dimethyl-3,4-dihydro-2H-benzo[b][1,4]thiazine-6-carboxamide | [M + H]+ = 381.1 |
| 70 | 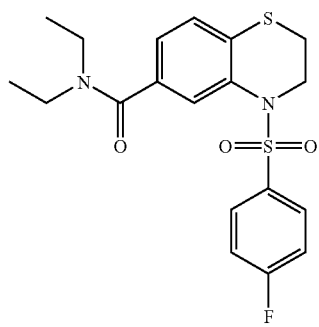 | N,N-diethyl-4-(4-fluorophenylsulfonyl)-3,4-dihydro-2H-benzo[b][1,4]thiazine-6-carboxamide | [M + H]+ = 409.0 |
| 71 | 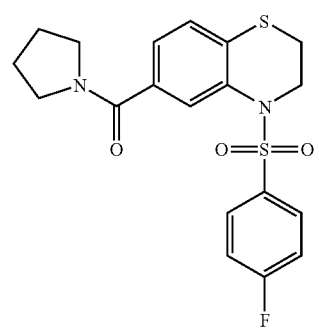 | 4-(4-fluorophenylsulfonyl)-3,4-dihydro-2H-benzo[b][1,4]thiazin-6-yl)(pyrrolidin-1-yl)methanone | [M + H]+ = 407.0 |

TABLE 5-continued

| Example | Compound | Name | MS |
|---|---|---|---|
| 72 | | N,N-dimethyl-4-(4-(trifluoromethyl)phenylsulfonyl)-3,4-dihydro-2H-benzo[b][1,4]thiazine-6-carboxamide | [M + H]$^+$ = 431.1 |
| 73 | | N,N-diethyl-4-(4-(trifluoromethyl)phenylsulfonyl)-3,4-dihydro-2H-benzo[b][1,4]thiazine-6-carboxamide | [M + H]$^+$ = 459.0 |
| 74 | | pyrrolidin-1-yl(4-(4-(trifluoromethyl)phenylsulfonyl)-3,4-dihydro-2H-benzo[b][1,4]thiazin-6-yl)methanone | [M + H]$^+$ = 457.0 |
| 75 | | piperidin-1-yl(4-(4-(trifluoromethyl)phenylsulfonyl)-3,4-dihydro-2H-benzo[b][1,4]thiazin-6-yl)methanone | [M + H]$^+$ = 471.0 |

TABLE 5-continued

| Example | Compound | Name | MS |
|---|---|---|---|
| 76 | | morpholino(4-(4-(trifluoromethyl)phenylsulfonyl)-3,4-dihydro-2H-benzo[b][1,4]thiazin-6-yl)methanone | [M + H]⁺ = 473.0 |
| 77 | | 4-(4-fluorophenylsulfonyl)-3,4-dihydro-2H-benzo[b][1,4]thiazin-6-yl)(piperidin-1-yl)methanone | [M + H]⁺ = 421.0 |
| 78 | | N'-benzoyl-4-(4-fluorophenylsulfonyl)-3,4-dihydro-2H-benzo[b][1,4]thiazine-6-carbohydrazide | [M + H]⁺ = 472.5 |
| 79 | | N'-benzoyl-4-(4-(trifluoromethyl)phenylsulfonyl)-3,4-dihydro-2H-benzo[b][1,4]thiazine-6-carbohydrazide | [M + H]⁺ = 522.0 |

Example 80

Preparation of 3-(3-(trifluoromethyl)phenyl)-5-(4-(4-(trifluoromethyl)phenylsulfonyl)-3,4-dihydro-2H-benzo[b][1,4]thiazin-6-yl)-1,2,4-oxadiazole

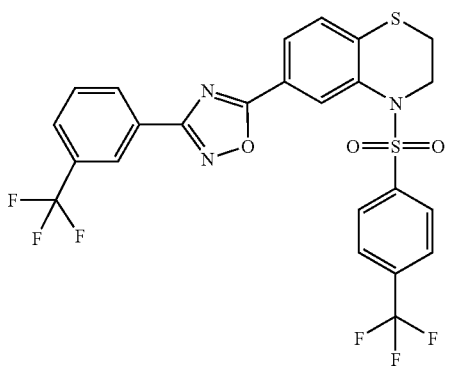

Step 1: Preparation of 3-(trifluoromethyl)-N'-(4-(4-(trifluoromethyl)phenylsulfonyl)-3,4-dihydro-2H-benzo[b][1,4]thiazine-6-carbonyloxy)benzimidamide To a solution of Intermediate L (26.5 mg, 0.066 mmol) in DMF (0.5 mL) was added EDCI (19.1 mg, 0.1 mmol), HOBT (15.3 mg, 0.1 mmol), N'-hydroxy-3-(trifluoromethyl)benzimidamide (171 μL, 0.085 mmol). The reaction was allowed to stir at room temperature for 16 hours. The reaction mixture was diluted with EtOAc (1 mL) and water (1 mL). The layers were separated and the aqueous layer was washed with EtOAc (1 mL). The combined organic layers were washed with 1M NaOH (1 mL), brine, dried over $Na_2SO_4$ and concentrated in vacuo to provide an orange solid. The material was used without purification.

Step 2: Preparation of 3-(3-(trifluoromethyl)phenyl)-5-(4-(4-(trifluoromethyl)phenylsulfonyl)-3,4-dihydro-2H-benzo[b][1,4]thiazin-6-yl)-1,2,4-oxadiazole 3-(trifluoromethyl)-N'-(4-(4-(trifluoromethyl)phenylsulfonyl)-3,4-dihydro-2H-benzo[b][1,4]thiazine-6-carbonyloxy)benzimidamide (38.8 mg, 0.066 mmol) was dissolved in THF (0.5 mL) and 1.0M TBAF/THF (0.5 mL, 0.5 mmol). The reaction was allowed to stir at room temperature for 16 hours. The reaction mixture was diluted with EtOAc (1 mL) and water (1 mL). The layers were separated and the aqueous layer was washed with EtOAc (1 mL). The combined organic layers were washed with brine, dried over $Na_2SO_4$ and concentrated in vacuo. The resulting residue was purified by flash column chromatography using a gradient elution of hexanes with 10-60% EtOAc to provide 3-(3-(trifluoromethyl)phenyl)-5-(4-(4-(trifluoromethyl)phenylsulfonyl)-3,4-dihydro-2H-benzo[b][1,4]thiazin-6-yl)-1,2,4-oxadiazole (17.6 mg, 0.031 mmol, 45% yield) as a yellow oil. LCMS (+ESI) m/z=572.05 [M+H]$^+$. The compounds listed in Table 6 were prepared using the procedure outlined in the synthesis of the compound of Example 80. These compounds can be prepared from the appropriate intermediate (selected from Intermediates J to L) by treatment with the appropriate amine under the above-described conditions.

TABLE 6

| Example | Compound | Name | MS |
|---------|----------|------|-----|
| 81 | | 3-(pyridin-2-yl)-5-(4-(4-(trifluoromethyl)phenylsulfonyl)-3,4-dihydro-2H-benzo[b][1,4]thiazin-6-yl)-1,2,4-oxadiazole | [M + H]$^+$ = 505.0 |
| 82 | | 3-tert-butyl-5-(4-(4-(trifluoromethyl)phenylsulfonyl)-3,4-dihydro-2H-benzo[b][1,4]thiazin-6-yl)-1,2,4-oxadiazole | [M + H]$^+$ = 484.0 |

TABLE 6-continued

| Example | Compound | Name | MS |
|---|---|---|---|
| 83 | | 5-(4-(4-fluorophenylsulfonyl)-3,4-dihydro-2H-benzo[b][1,4]thiazin-6-yl)-3-(pyridin-2-yl)-1,2,4-oxadiazole | [M + H]+ = 455.0 |
| 84 | | 3-tert-butyl-5-(4-phenylsulfonyl)-3,4-dihydro-2H-benzo[b][1,4]thiazin-6-yl)-1,2,4-oxadiazole | [M + H]+ = 416.0 |
| 85 | | 3-tert-butyl-5-(4-(4-fluorophenylsulfonyl)-3,4-dihydro-2H-benzo[b][1,4]thiazin-6-yl)-1,2,4-oxadiazole | [M + H]+ = 434.0 |
| 86 | | 3-ethyl-5-(4-phenylsulfonyl)-3,4-dihydro-2H-benzo[b][1,4]thiazin-6-yl)-1,2,4-oxadiazole | [M + H]+ = 388.1 |

TABLE 6-continued

| Example | Compound | Name | MS |
|---------|----------|------|-----|
| 87 | | 5-(4-(phenylsulfonyl)-3,4-dihydro-2H-benzo[b][1,4]thiazin-6-yl)-3-(pyridin-2-yl)-1,2,4-oxadiazole | [M + H]⁺ = 437.0 |
| 88 | | 5-(4-(4-fluorophenylsulfonyl)-3,4-dihydro-2H-benzo[b][1,4]thiazin-6-yl)-3-(3-(trifluoro-methyl)phenyl)-1,2,4-oxadiazole | [M + H]⁺ = 522.0 |
| 89 | | 3-ethyl-5-(4-(4-(trifluoromethyl)phenylsulfonyl)-3,4-dihydro-2H-benzo[b][1,4]thiazin-6-yl)-1,2,4-oxadiazole | [M + H]⁺ = 456.0 |
| 90 | | 3-ethyl-5-(4-(4-fluorophenylsulfonyl)-3,4-dihydro-2H-benzo[b][1,4]thiazin-6-yl)-1,2,4-oxadiazole | [M + H]⁺ = 406.0 |

Example 91

Preparation of N-tert-butyl-2,2-dimethyl-5-(phenylsulfonyl)-2,3,4,5-tetrahydrobenzo[b][1,4]thiazepine-7-carboxamide

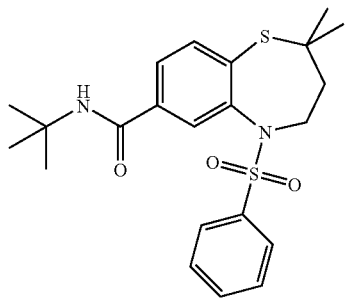

Step 1: Preparation of 2,2-dimethyl-5-(phenylsulfonyl)-2,3,4,5-tetrahydrobenzo[b][1,4]-thiazepine-7-carbonyl chloride To a solution of 2,2-dimethyl-5-(phenylsulfonyl)-2,3,4,5-tetrahydrobenzo[b][1,4]-thiazepine-7-carboxylic acid (480 mg, 1.272 mmol) in DCE (20 mL) was added thionyl chloride (2 mL, 27.4 mmol). The reaction was heated to 70° C. and stirred at that temperature for 2 hours. LCMS analysis of the reaction mixture indicated consumption of starting material. The solvent was removed under reduced pressure and 2,2-dimethyl-5-(phenylsulfonyl)-2,3,4,5-tetrahydrobenzo[b][1,4]thiazepine-7-carbonyl chloride (500 mg, 1.263 mmol, 99% yield) was used without further purification.

Step 2: Preparation of N-tert-butyl-2,2-dimethyl-5-(phenylsulfonyl)-2,3,4,5-tetrahydrobenzo[b][1,4]thiazepine-7-carboxamide To a biphasic mixture of 2,2-dimethyl-5-(phenylsulfonyl)-2,3,4,5-tetrahydrobenzo[b][1,4]thiazepine-7-carbonyl chloride (30 mg, 0.076 mmol) in DCM (2 mL) and saturated aqueous NaHCO$_3$ (2 mL) was added tert-butylamine (25 µL, 0.236 mmol). The reaction was stirred at room temperature for 72 hours. TLC analysis of the reaction mixture indicated consumption of starting material. The biphasic mixture was extracted with DCM (3×2 mL). The combined organics were dried over Na$_2$SO$_4$ and concentrated in vacuo. The resulting solid was purified by flash column chromatography using a gradient elution of Hexanes with 5-50% EtOAc to provide N-tert-butyl-2,2-dimethyl-5-(phenylsulfonyl)-2,3,4,5-tetrahydrobenzo[b][1,4]thiazepine-7-carboxamide (26.3 mg, 0.052 mmol, 68.2% yield) as an off white solid. LCMS (+ESI) m/z=432.9 [M+H]$^+$; $^1$H-NMR (CDCl$_3$) δ 7.73-7.70 (m, 2H), 7.68-7.63 (m, 2H), 7.55 (tt, 1H), 7.49 (d, 1H), 7.47-7.41 (m, 2H), 5.89 (s, 1H), 3.77 (br s, 1H), 1.88 (br s, 2H), 1.46 (s, 9H), 1.12 (br s, 6H).

The compounds listed in Table 7 were prepared using the procedure outlined in the synthesis of the compound of Example 91. These compounds can be prepared from the appropriate intermediate (selected from intermediates O and P) by treatment with the appropriate amine in step 2 under the above-described conditions.

TABLE 7

| Example | Compound | Name | MS |
| --- | --- | --- | --- |
| 92 | | N-isobutyl-2,2-dimethyl-5-(phenyl-sulfonyl)-2,3,4,5-tetrahydrobenzo[b][1,4]thiazepine-7-carboxamide | [M + H]$^+$ = 432.9 |
| 93 | | (2,2-dimethyl-5-(phenylsulfonyl)-2,3,4,5-tetrahydrobenzo[b][1,4]thiazepin-7-yl)(piperidin-1-yl)methanone | [M + H]$^+$ = 444.9 |

TABLE 7-continued

| Example | Compound | Name | MS |
|---------|----------|------|----|
| 94 | | (2,2-dimethyl-5-(phenylsulfonyl)-2,3,4,5-tetrahydro-benzo[b][1,4]thiazepin-7-yl)(morpholino)-methanone | [M + H]⁺ = 446.9 |
| 95 | | (S)-methyl 2-(2,2-dimethyl-5-(phenyl-sulfonyl)-2,3,4,5-tetrahydrobenzo[b][1,4]thiazepine-7-carboxamido)-3,3-dimethylbutanoate | [M + H]⁺ = 504.9 |
| 96 | | 2,2-dimethyl-N-neo-pentyl-5-(phenyl-sulfonyl)-2,3,4,5-tetrahydrobenzo[b][1,4]thiazepine-7-carboxamide | [M + H]⁺ = 446.9 |
| 97 | | (R)-N-(3,3-dimethyl-butan-2-yl)-2,2-dimethyl-5-(phenyl-sulfonyl)-2,3,4,5-tetrahydrobenzo[b][1,4]thiazepine-7-carboxamide | [M + H]⁺ = 460.9 |
| 98 | | (S)-N-(3,3-dimethyl-butan-2-yl)-2,2-dimethyl-5-(phenyl-sulfonyl)-2,3,4,5-tetrahydrobenzo[b][1,4]thiazepine-7-carboxamide | [M + H]⁺ = 460.9 |

TABLE 7-continued

| Example | Compound | Name | MS |
| --- | --- | --- | --- |
| 99 | | 5-(4-fluorophenyl-sulfonyl)-2,2-dimethyl-N-((tetrahydro-2H-pyran-4-yl)methyl)-2,3,4,5-tetrahydro-benzo[b][1,4]thiazepine-7-carboxamide | [M + H]$^+$ = 492.9 |
| 100 | | (5-(4-fluorophenyl-sulfonyl)-2,2-dimethyl-2,3,4,5-tetrahydro-benzo[b][1,4]thiazepin-7-yl)(morpholino)-methanone | [M + H]$^+$ = 464.8 |
| 101 | | N-cyclopentyl-5-(4-fluorophenylsulfonyl)-2,2-dimethyl-2,3,4,5-tetrahydrobenzo[b][1,4]thiazepine-7-carboxamide | [M + H]$^+$ = 462.9 |
| 102 | | (5-(4-fluorophenyl-sulfonyl)-2,2-dimethyl-2,3,4,5-tetrahydro-benzo[b][1,4]thiazepin-7-yl)(pyrrolidin-1-yl)-methanone | [M + H]$^+$ = 448.9 |

TABLE 7-continued

| Example | Compound | Name | MS |
|---|---|---|---|
| 103 | | (S)-N-(3,3-dimethyl-1-(methylamino)-1-oxobutan-2-yl)-5-(4-fluorophenyl-sulfonyl)-2,2-dimethyl-2,3,4,5-tetrahydrobenzo-[b][1,4]thiazepine-7-carboxamide | [M + H]+ = 521.9 |

Example 104

Preparation of 2-(4-(4-fluorophenylsulfonyl)-3,4-dihydro-2H-benzo[b][1,4]thiazin-6-yl)-5-phenyl-1,3,4-oxadiazole

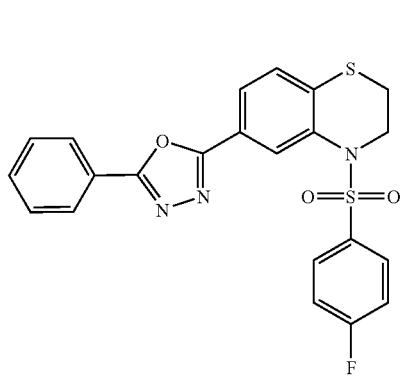

To a solution of Example 78 (20 mg, 42 µmol) in THF (1 mL) was added DBU (10 mg, 64 µmol) and Burgess reagent (50.5 mg, 212 µmol). The reaction vial was capped subjected to microwave irradiation (150° C., 5 min). Analysis of the reaction mixture indicated the presence of starting material, so additional burgess reagent (10.1 mg, 42 µmol) was added and the reaction mixture was resubjected to microwave irradiation (150° C., 10 min). LCMS analysis of the reaction mixture indicated consumption of starting material. The reaction was diluted with saturated aqueous sodium bicarbonate (1 mL) and EtOAc (2 mL). The organic layer was removed and the aqueous layer extracted with EtOAc (2 mL). The combined were dried over anhydrous $Na_2SO_4$, filtered and concentrated in vacuo. The resulting residue was purified by flash column chromatography using a gradient elution of hexanes with 10-60% EtOAc to provide 2-(4-(4-fluorophenylsulfonyl)-3,4-dihydro-2H-benzo[b][1,4]thiazin-6-yl)-5-phenyl-1,3,4-oxadiazole (1 mg, 2.2 µmol, 5% yield). LCMS (+ESI) m/z=454.5 [M+H]+; $^1$H-NMR (CDCl$_3$) δ 8.0-8.1 (m, 5H), 7.4-7.5 (m, 5H), 7.25 (d, 1H), 7.00 (dd, 1H), 6.76 (d, 1H), 3.53 (t, 2H), 3.08 (t, 2H).

Example 105

Preparation of 2-phenyl-5-(4-(4-(trifluoromethyl)phenylsulfonyl)-3,4-dihydro-2H-benzo[b][1,4]thiazin-6-yl)-1,3,4-oxadiazole

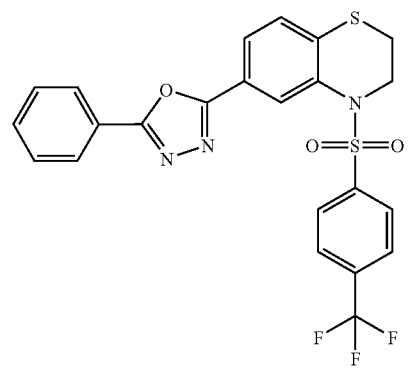

This compound was prepared using the procedure outlined in the synthesis of Example 104, with substitution of Example 79 for Example 78. LCMS (+ESI) m/z=504.0 [M+H]+.

Example 106

Preparation of 2-methyl-5-(4-(1-methyl-1H-imidazol-4-ylsulfonyl)-3,4-dihydro-2H-benzo[b][1,4]thiazin-6-yl)-1,3,4-oxadiazole

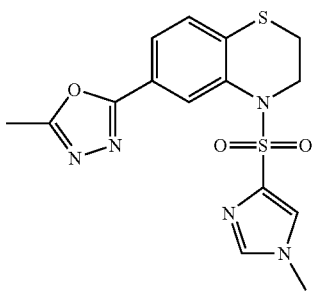

Step 1: Preparation of N'-acetyl-4-(1-methyl-1H-imidazol-4-ylsulfonyl)-3,4-dihydro-2H-benzo[b][1,4]thiazine-6-carbohydrazide To a solution of intermediate M (77 mg, 226 μmol) in DMF (2 mL) was added acetohydrazide (18 mg, 249 μmol), DIPEA (80 μL, 453 μmol) and TBTU (80 mg, 249 μmol), The reaction was allowed to stir at room temperature for 3 hours. LCMS analysis of the reaction mixture indicated that the starting material had been consumed. The reaction was quenched with saturated aqueous $NaHCO_3$ (2 mL) and extracted with EtOAc (2×2 mL). The organic layers were combined, dried over anhydrous $Na_2SO_4$, filtered and concentrated in vacuo. The residue was purified by flash column chromatography with a gradient elution of hexanes and 25-100% EtOAc to provide N'-acetyl-4-(1-methyl-1H-imidazol-4-ylsulfonyl)-3,4-dihydro-2H-benzo[b][1,4]thiazine-6-carbohydrazide (71 mg, 180 μmol, 80% yield). LCMS (+ESI) m/z=395.8 [M+H]⁻.

Step 2: Preparation of 2-methyl-5-(4-(1-methyl-1H-imidazol-4-ylsulfonyl)-3,4-dihydro-2H-benzo[b][1,4]thiazin-6-yl)-1,3,4-oxadiazole To a solution of N'-acetyl-4-(1-methyl-1H-imidazol-4-ylsulfonyl)-3,4-dihydro-2H-benzo[b][1,4]thiazine-6-carbohydrazide (25 mg, 63 μmol) in THF (1 mL) was added DBU (14 mg, 95 μmol) and Burgess reagent (75 mg, 316 μmol). The reaction vial was capped subjected to microwave irradiation (150° C., 10 min). LCMS analysis of the reaction mixture indicated that the starting material had been consumed. The reaction was diluted with saturated aqueous $NaHCO_3$ (1 mL) and EtOAc (2 mL). The organic layer was removed and the aqueous layer was extracted with EtOAc (2 mL). The organic layers were combined, dried over anhydrous $Na_2SO_4$, filtered and concentrated in vacuo. The residue was purified by flash column chromatography with a gradient elution of hexanes with 10-60% EtOAc to provide 2-methyl-5-(4-(1-methyl-1H-imidazol-4-ylsulfonyl)-3,4-dihydro-2H-benzo[b][1,4]thiazin-6-yl)-1,3,4-oxadiazole (16 mg, 42 μmol, 67% yield). LCMS (+ESI) m/z=377.8 [M+H]⁺; ¹H-NMR (CDCl₃) δ 8.05 (m, 2H), 7.9 (d, 2H), 7.8 (d, 2H), 7.4-7.5 (m, 3H), 7.25 (d, 1H), 7.1 (dd, 1H), 6.75 (d, 1H), 3.5 (t, 2H), 3.1 (t, 2H).

Example 107

Preparation of 6-(5-phenyl-1H-imidazol-2-yl)-4-(4-(trifluoromethyl)phenylsulfonyl)-3,4-dihydro-2H-benzo[b][1,4]thiazine

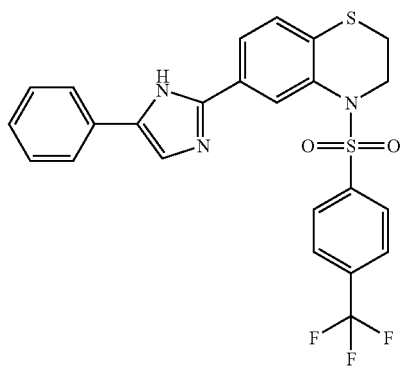

Step 1: Preparation of 4-(4-(trifluoromethyl)phenyl-sulfonyl)-3,4-dihydro-2H-benzo[b][1,4]thiazine-6-carbonyl chloride To a solution of Intermediate L (50 mg, 124 μmol) in DCM (5 mL) at 0° C. was added oxalyl chloride (21 μL, 248 μmol) and catalytic DMF (5 μL). Upon addition of DMF vigorous gas evolution was observed. The reaction stirred at 0° C. 1 h, then warmed to room temperature and allowed to stir for an additional 1.5 hours. The reaction mixture was concentrated under reduced pressure to provide the acid chloride, which was used without purification.

Step 2: Preparation of N-(2-oxo-2-phenylethyl)-4-(4-(trifluoromethyl)-phenylsulfonyl)-3,4-dihydro-2H-benzo[b][1,4]thiazine-6-carboxamide To a solution of the residue from Step 1 in THF (1 mL) was added 2-amino-1-phenylethanone (19 mg, 136 μmol) and DIPEA (108 μL, 620 μmol). The reaction was allowed to stir at room temperature for 2 hours. LCMS analysis of the reaction mixture indicated complete consumption of starting material. The reaction concentrated in vacuo and the residue partitioned between DCM (2 mL) and saturated aqueous sodium bicarbonate (2 mL). The layers were separated and the aqueous layer was extracted with DCM (2 mL). The combined organic layers were dried over anhydrous $Na_2SO_4$, filtered and concentrated in vacuo to provide N-(2-oxo-2-phenylethyl)-4-(4-(trifluoromethyl)phenyl-sulfonyl)-3,4-dihydro-2H-benzo[b][1,4]thiazine-6-carboxamide (40 mg, 76.9 μmol, 62% yield) as a yellow oil, which was used without further purification. LCMS (+ESI) m/z=521.5 [M+H]⁺.

Step 3: Preparation of 6-(5-phenyl-1H-imidazol-2-yl)-4-(4-(trifluoro-methyl)phenyl-sulfonyl)-3,4-dihydro-2H-benzo[b][1,4]thiazine To a solution of N-(2-oxo-2-phenylethyl)-4-(4-(trifluoromethyl)phenylsulfonyl)-3,4-dihydro-2H-benzo[b][1,4]thiazine-6-carboxamide (20 mg, 38 μmol) in DMF (1 mL) was added ammonium acetate (30 mg, 380 μmol). The reaction mixture was subjected to microwave irradiation (150° C., 15 min). LCMS analysis of the reaction mixture indicated nearly complete conversion of the starting material. The reaction mixture diluted with saturated aqueous sodium bicarbonate (1 mL) and EtOAc (2 mL). The organic layer was removed and the aqueous layer extracted with EtOAc (2 mL). The combined organic layers were dried over anhydrous $Na_2SO_4$, filtered and concentrated in vacuo. The resulting residue was purified by flash column chromatography using a gradient elution of hexanes with 10-60% EtOAc to provide 6-(5-phenyl-1H-imidazol-2-yl)-4-(4-(trifluoro-methyl)phenylsulfonyl)-3,4-dihydro-2H-benzo[b][1,4]thiazine (1.2 mg, 2.4 μmol, 6% yield) as a yellow oil. LCMS (+ESI) m/z=502.5 [M+H]⁺; ¹H-NMR (CDCl₃) δ 8.10 (m, 2H), 7.90 (d, 2H), 7.80 (d, 2H), 7.4-7.5 (m, 4H), 7.25 (d, 1H), 7.00 (dd, 1H), 6.76 (d, 1H), 3.53 (t, 2H), 3.08 (t, 2H).

Example 108

Preparation of 4-(4-fluorophenylsulfonyl)-6-(5-phenyl-1H-imidazol-2-yl)-3,4-dihydro-2H-benzo[b][1,4]thiazine

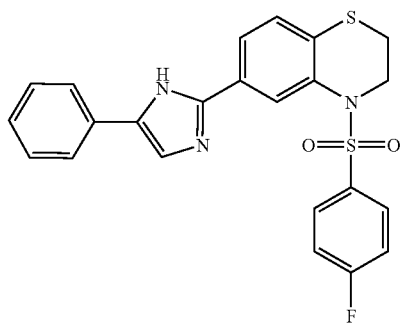

This compound was prepared using the procedure outlined in the synthesis of Example 107, with substitution of Intermediate J for Intermediate L. LCMS (+ESI) m/z=452.0 [M+H]⁺.

Example 109

Preparation of 2-(4-(4-(trifluoromethyl)phenylsulfonyl)-3,4-dihydro-2H-benzo[b][1,4]thiazin-6-yl)benzo[d]oxazole

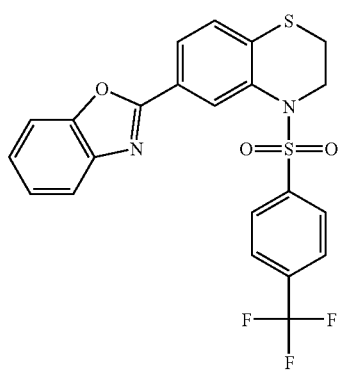

Step 1: Preparation of N-(2-hydroxyphenyl)-4-(4-(trifluoromethyl)-phenylsulfonyl)-3,4-dihydro-2H-benzo[b][1,4]thiazine-6-carboxamide To a solution of intermediate Example 107 Step 1 (52 mg, 124 µmol) in THF (1 mL) was added 2-aminophenol (15 mg, 136 µmol) and the DIPEA (108 µL, 620 µmol). The reaction was allowed to stir at room temperature for 2 h. LCMS analysis of the reaction mixture indicated complete consumption of starting material. The solvent was removed under reduced pressure and the residue was partitioned between DCM (2 mL) and saturated aqueous sodium bicarbonate (2 mL). The organic layer was removed and the aqueous re-extracted with DCM (2 mL). The combined organics were dried over anhydrous Na₂SO₄, filtered and concentrated in vacuo. N-(2-hydroxyphenyl)-4-(4-(trifluoromethyl)phenylsulfonyl)-3,4-dihydro-2H-benzo[b][1,4]thiazine-6-carboxamide (42 mg, 85 µmol, 68% yield) was obtained as a yellow oil and was used without further purification. LCMS (+ESI) m/z=495.4 [M+H]⁺.

Step 2: Preparation of 2-(4-(4-(trifluoromethyl)phenylsulfonyl)-3,4-dihydro-2H-benzo[b][1,4]thiazin-6-yl)benzo[d]oxazole N-(2-hydroxyphenyl)-4-(4-(trifluoromethyl)phenylsulfonyl)-3,4-dihydro-2H-benzo[b][1,4]thiazine-6-carboxamide (25 mg, 51 µmol) was dissolved in 1 mL of DMF. Ammonium acetate (39 mg, 506 µmol) was added and the reaction was subjected to microwave irradiation (150° C., 25 min). LCMS analysis of the reaction mixture showed consumption of starting material. The reaction mixture was diluted with saturated aqueous sodium bicarbonate (1 mL) and EtOAc (2 mL). The organic layer was removed and the aqueous layer extracted with EtOAc (2 mL). The organic layers were combined, dried over anhydrous Na₂SO₄, filtered and evaporated. The residue was purified by flash column chromatography with gradient elution of hexanes with 10-60% EtOAc to provide 2-(4-(4-(trifluoromethyl)phenylsulfonyl)-3,4-dihydro-2H-benzo[b][1,4]thiazin-6-yl)benzo[d]oxazole (1.4 mg, 2.9 µmol, 6% yield) as a yellow oil. LCMS (+ESI) m/z=477.4 [M+H]⁺; ¹H-NMR (CDCl₃) δ 7.7-7.9 (m, 6H), 7.40 (d, 2H), 7.30 (d, 1H), 7.05 (dd, 1H), 6.80 (d, 1H), 3.50 (t, 2H), 3.05 (t, 2H).

Example 110

Preparation of 4-benzoyl-N-isopropyl-3,4-dihydro-1,1-dioxo-2H-benzo[b][1,4]thiazine-6-carboxamide

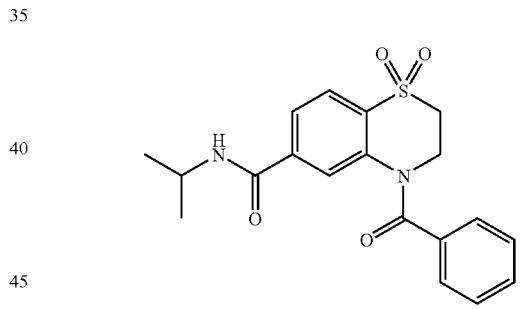

To a solution of the compound of Example 26 (4 mg, 0.012 mmol) in DCM (1 ml) was added mCPBA (2.028 mg, 0.012 mmol). The reaction was allowed to stir for 30 min. LCMS indicated that the reaction was complete. The reaction was then quenched with saturated aqueous NaHCO₃ and the reaction mixture was extracted with DCM (3×2 mL). The combined organics were dried over Na₂SO₄ and concentrated in vacuo. The mixture was purified by flash column chromatography and eluted with a gradient of hexanes with 5-60% EtOAc in hexanes to provide the desired compound, 4-benzoyl-N-isopropyl-3,4-dihydro-1,1-dioxo-2H-benzo[b][1,4]thiazine-6-carboxamide (3.9 mg, 0.0010 mmol, 89% yield) as a white solid. LCMS (+ESI) m/z=373.2 [M+H]⁺.

Screening Methods

The ability of compounds to act as agonists or inverse agonists at human CB2 and CB1 receptors (hCB2, hCB1, respectively) and at the rat CB2 receptor (rCB2) was determined by measuring changes in intracellular cAMP levels. Chinese Hamster Ovary (CHO-K1) cell lines stably expressing hCB2 (Genebank: X74328) or hCB1 (Genebank:

X54937) were purchased from Euroscreen (Gosselies, Belgium). The rat CB2 receptor was expressed from genomic DNA (provided by M. Abood, California Pacific Medical Center) in CHO-K1 cells from expression plasmid vector, pcDNA3.1.

Cell lines were grown in suspension in EX-CELL 302 CHO Serum-free medium (Sigma, cat #14324C) supplemented with 1% Fetal Bovine Serum, glutamine and non-essential amino-acids under 0.4 mg/mL G418 selection.

Receptor mediated responses were determined by measuring changes in intracellular cAMP using LANCE cAMP detection kit (cat #AD0264, Perkin Elmer, Wellesley, Mass.) based on time-resolved fluorescence resonance energy transfer (TR-FRET). Changes in cAMP were determined in cells pre-incubated with IBMX (isobutyl methylxanthine) and pre-stimulated with NKH-477 (a water soluble forskolin derivative, cat #1603, Tocris, Ellisville, Mo.) to increase basal cAMP levels as detailed below.

On the day of the experiment, cells were spun at low speed for 5 min at room temperature. The supernatant was removed and cells were resuspended in stimulation buffer (Hanks Buffered Salt Solution/5 mM HEPES, containing 0.5 mM IBMX (cat #17018, Sigma) and 0.02% BSA (Perkin-Elmer, cat #CR84-100)). Cell clumps were removed by filtering through cell strainer 40 μm (BD Falcon, Discovery Labware, Bedford, Mass.) and diluted to $2 \times 10^5$ cells/mL. Antibody supplied with the LANCE cAMP immunoassay kit was then added according to the manufacturer's instructions. An aliquot of cells was taken for un-induced controls. To the remaining cells was added NKH-477 (a water soluble forskolin derivative, Tocris cat #1603) to a final concentration of 2-8 μM. Cells were then incubated for 30 min at room temperature prior to adding to Proxiplates containing test compounds (final DMSO concentration was less than 0.5%) with a Multidrop bulk dispenser, followed by 60 minutes incubation at room temperature. The response was stopped by addition of the detection mix supplied with the LANCE kit.

The reagents were allowed to equilibrate for 3 hours prior to reading on an Envision multi-mode detector (Perkin-Elmer). TR-FRET was measured using a 330-380 nm excitation filter, a 665 nm emission filter, dichroic mirror 380 nm and Z=1 mm.

Cyclic AMP concentrations in each well were back-calculated from a cAMP standard curve run concurrently during each assay. Each plate contained 16 wells of forskolin stimulated cells and 16 wells of forskolin plus CP55,940-treated cells. Cells were treated with 1 μM CP55,940 (Tocris cat. #0949). Concentrations of cAMP were expressed as a percent of the difference of these two groups of wells. Concentration-response data including $EC_{50}$ (the concentration of compound producing 50% of the maximal response) and intrinsic activity (the percent maximal activation compared to full activation by CP55,940) were determined using a four-parameter non-linear regression algorithm (Xlfit equation 251, IDBS).

Example 111

Determination of $EC_{50}$ Values for Compounds 1-110

Table 8 shows the $EC_{50}$ ranges of compounds as determined by the above method when tested against the human CB2, rat CB2 and human CB1 receptors, respectively.

TABLE 8

| Example | hCB2 | rCB2 | hCB1 |
|---------|------|------|------|
| 1 | −E | AR | −E |
| 2 | −E | −C | −E |
| 3 | AR | −E | −E |
| 4 | −E | AR | −E |
| 5 | −E | −E | −E |
| 6 | AR | −E | −E |
| 7 | AR | −E | −E |
| 8 | AR | AR | −E |
| 9 | AR | −D | AR |
| 10 | +D | +D | AR |
| 11 | −E | −D | AR |
| 12 | AR | −D | −E |
| 13 | AR | AR | AR |
| 14 | −E | −D | −E |
| 15 | AR | −E | AR |
| 16 | −E | −D | AR |
| 17 | AR | −E | AR |
| 18 | −E | −E | AR |
| 19 | −E | −E | AR |
| 20 | −E | AR | AR |
| 21 | −E | −D | −E |
| 22 | −E | −D | −E |
| 23 | −E | −D | −E |
| 24 | −E | −D | −E |
| 25 | −E | −D | −E |
| 26 | AR | −E | AR |
| 27 | +E | +D | AR |
| 28 | AR | AR | AR |
| 29 | +D | +D | AR |
| 30 | −E | −E | AR |
| 31 | AR | AR | AR |
| 32 | AR | −E | AR |
| 33 | +D | AR | AR |
| 34 | +D | +D | AR |
| 35 | +E | −E | AR |
| 36 | +E | −E | AR |
| 37 | +E | −E | AR |
| 38 | AR | −E | AR |
| 39 | AR | −E | −E |
| 40 | +D | −D | −E |
| 41 | +C | +A | AR |
| 42 | +D | +C | +E |
| 43 | +B | +A | +D |
| 44 | +C | +B | AR |
| 45 | +B | +A | +D |
| 46 | +B | +B | AR |
| 47 | +B | +A | +E |
| 48 | +D | +B | AR |
| 49 | +C | +A | +E |
| 50 | AR | AR | AR |
| 51 | AR | −C | +D |
| 52 | +C | +A | AR |
| 53 | +E | +D | AR |
| 54 | +E | +D | AR |
| 55 | +E | +D | AR |
| 56 | AR | +E | AR |
| 57 | +E | +D | AR |
| 58 | +B | +A | +D |
| 59 | +C | +C | AR |
| 60 | +B | +B | +D |
| 61 | +C | +C | +E |
| 62 | +B | +A | +D |
| 63 | +B | +A | +D |
| 64 | AR | AR | AR |
| 65 | +C | +C | AR |
| 66 | +D | +D | AR |
| 67 | +D | +C | AR |
| 68 | +D | +D | AR |
| 69 | +E | +D | AR |
| 70 | +D | +C | AR |
| 71 | +C | +C | +E |
| 72 | +C | +C | AR |
| 73 | +C | +C | +E |
| 74 | +E | −C | AR |
| 75 | AR | −C | AR |
| 76 | +D | +C | AR |
| 77 | +C | +C | +E |
| 78 | +E | +D | AR |

TABLE 8-continued

| Example | hCB2 | rCB2 | hCB1 |
|---|---|---|---|
| 79 | +D | +D | AR |
| 80 | +D | AR | AR |
| 81 | +B | +A | AR |
| 82 | +B | +B | +D |
| 83 | +C | +B | +D |
| 84 | +C | +A | +E |
| 85 | +B | +B | +D |
| 86 | +B | +A | AR |
| 87 | AR | AR | AR |
| 88 | AR | AR | AR |
| 89 | +B | +A | +D |
| 90 | +B | +A | +D |
| 91 | +D | +B | −E |
| 92 | AR | −E | −E |
| 93 | AR | +C | −E |
| 94 | +E | +D | AR |
| 95 | +D | AR | −D |
| 96 | +D | AR | −D |
| 97 | +D | AR | −D |
| 98 | +D | −E | −D |
| 99 | AR | −C | −E |
| 100 | +E | +C | −E |
| 101 | +E | −C | −E |
| 102 | AR | +C | AR |
| 103 | +D | +C | −E |
| 104 | +C | +B | +D |
| 105 | +C | +A | +D |
| 106 | +E | +D | AR |
| 107 | +C | +B | AR |
| 108 | +C | +B | +E |
| 109 | +C | +B | +D |
| 110 | AR | AR | AR |

AR: Above assay range;
A: $EC_{50}$ in the range 0.1-1.0 nM;
B: $EC_{50}$ in the range 1.01 nM-10.0 nM;
C: $EC_{50}$ in the range 10.1 nM-100 nM;
D: $EC_{50}$ in the range 101 nM-1.0 μM;
E: $EC_{50}$ in the range 1.01 μM-10 μM;
"+" or "−": identifies the compound as an agonist or an inverse agonist, respectively.

Example 112

Anti-Hyperalgesia in an In Vivo Inflammatory Pain Model

The anti-hyperalgesic effects of test compounds in the Complete Freund's Adjuvant (CFA) model of inflammatory pain was examined as described below. Male Sprague-Dawley rats (Harlan) weighing 150-200 grams, were housed three to a cage. Animals had access to food and water ad libitum (except during testing) and were maintained on a 12 hours light: 12 hours dark cycle for the entire duration of the experiment. Test compounds were prepared in 50% DMSO (Sigma) in saline. The positive control was the mixed CB1/CB2 agonist WIN 55212,2 (Sigma). Local inflammation was induced by 50 uL CFA (Mycobacterium tuberculosis 1 mg/mL; Sigma) injected subcutaneously into the plantar surface of the right paw.

Assessment of mechanical hyperalgesia: Baseline and post-treatment withdrawal thresholds to a noxious mechanical stimulus were measured using the Randall-Selitto paw pressure apparatus (Ugo Basile). This apparatus generates a linearly increasing mechanical force. The stimulus is applied to the dorsal surface of the hind paws by a dome-shaped plastic tip placed between the 3rd and 4th metatarsus. To avoid tissue damage, a cut-off pressure was set at 260 grams. Mechanical thresholds were defined as the force in grams at the first obvious pain behavior, which includes paw withdrawal, struggle, and/or vocalization.

All test compounds were administered locally into the injured paw in a maximum dosing volume of 0.1 mL. Paw withdrawal thresholds were measured before and after CFA administration and then after intrapaw administration of test compound. The mean and standard error of the mean (SEM) were determined for the injured and normal paws for each treatment group. The results for WIN 55212,2 and compound 45 are show in Table 9, below. Administration of vehicle did not significantly alter the sensitivity of either paw. Further, test compound administration did not significantly alter the paw withdrawal thresholds of the contralateral paw. No side effects were observed during the course of the experiment.

TABLE 9

| Compound # (dose) | Pre-CFA Threshold (g) | Post-CFA Threshold (g) | Test Threshold (g) |
|---|---|---|---|
| WIN 55212, 2 (0.1 mg/paw) | 175 ± 4 | 100 ± 3 | 255 ± 5* |
| 45 (1 mg/paw) | 175 ± 4 | 100 ± 3 | 179 ± 19* |

*denotes p < 0.05 compared to Post-CFA threshold

The texts of the references cited in this specification are herein incorporated by reference in their entireties. In the event that a definition of a term as incorporated by reference differs from the meaning defined herein, then the meaning provided herein is intended. The examples provided herein are for illustration purposes only and are not to be interpreted as limiting the scope of the invention, the full breadth of which will be immediately recognized by those of skill in the art.

We claim:

1. A compound of the structure of formula I

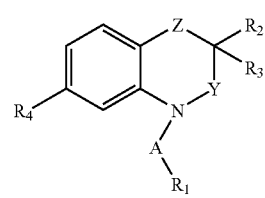

or a stereoisomer, racemate or salt thereof, wherein:
A is CO, CONH, or $SO_2$;
Y is $(CH_2)_p$;
Z is S, SO, or $SO_2$;
$R_1$ is (i) $C_1$-$C_6$ alkyl;
    (ii) aryl optionally substituted with from 1 to 3 substituents independently selected from group consisting of halogen, $C_1$-$C_6$ alkyl, $CF_3$, $OCF_3$, $OR_{10}$, $COR_{10}$, $COOR_{10}$, $NR_{10}R_{11}$, and $CONR_{10}R_{11}$;
    (iii) $C_3$-$C_8$ cycloalkyl; or
    (iv) 4- to 10-membered heterocyclyl, optionally substituted with from 1 to 3 substituents independently selected from the group consisting of halogen, $C_1$-$C_6$ alkyl, $C_1$-$C_6$ alkoxy, $CF_3$, $OCF_3$, $OR_{10}$, $COOR_{10}$, $NR_{10}R_{11}$, $COR_{10}$, and $CONR_{10}R_{11}$;
$R_2$ and $R_3$ are each independently H or $C_1$-$C_3$ alkyl;
$R_4$ is (i) $CONR_5R_6$; or
    (ii) aryl optionally substituted with from 1 to 3 substituents independently selected from the group consisting of halogen, $C_1$-$C_6$ alkyl, $C_1$-$C_6$ alkoxy, $CF_3$ and $OCF_3$;

$R_5$ and $R_6$ are defined by one of the following:
- (i) $R_5$ and $R_6$ are each independently selected from the group consisting of H, $C_1$-$C_6$ alkyl, $C_1$-$C_6$ alkoxyalkyl, $(CH_2)_m$-aryl, $(CH_2)_n$—$C_3$-$C_{10}$ cycloalkyl, and $(CH_2)_m$(3- to 8-membered heterocyclyl);
- (ii) $R_5$ is H or $C_1$-$C_6$ alkyl, and $R_6$ is $CR_7R_8R_9$ or —NH-$COR_{12}$; or
- (iii) $R_5$ and $R_6$, taken together with the nitrogen atom to which they are bonded, form a 4- to 10-membered heterocyclyl optionally substituted with from 1 to 3 substituents independently selected from the group consisting of halogen, $C_1$-$C_6$ alkyl, $C_1$-$C_6$ alkoxy, $CF_3$, $OCF_3$, $OR_{10}$, $COOR_{10}$, $NR_{10}R_{11}$, $COR_{10}$, and $CONR_{10}R_{11}$;

$R_7$ and $R_8$ are each independently H or $C_1$-$C_6$ alkyl, or $R_7$ and $R_8$, taken together with the carbon atom to which they are bonded, form a 3- to 6-membered carbocyclyl group or a 3- to 6-membered heterocyclyl;

$R_9$ is selected from the group consisting of $(CH_2)_p$—$OR_{13}$, $(CH_2)_p$—$NR_{13}R_{14}$, $(CH_2)_n COOR_{13}$, and $(CH_2)_n CONR_{13}R_{14}$;

each instance of $R_{10}$ is
- (i) independently selected from the group consisting of H, $C_1$-$C_6$ alkyl and $(CH_2)_n$—$C_3$-$C_8$ cycloalkyl; or
- (ii) independently aryl or heteroaryl optionally substituted with from 1 to 3 substituents independently selected from the group consisting of halogen, $CF_3$, $OCF_3$, $C_1$-$C_6$ alkyl, $C_1$-$C_6$ alkoxy;

each instance of $R_{11}$ is independently selected from the group consisting of H, $C_1$-$C_6$alkyl, and CO—($C_1$-$C_6$alkyl);

alternatively, $R_{10}$ and $R_{11}$, taken together with the nitrogen to which they are bonded, form a 5-6 membered heterocyclyl;

$R_{12}$ is (i) selected from the group consisting of $C_1$-$C_6$ alkyl, $C_1$-$C_6$ alkoxy, and $C_3$-$C_8$ cycloalkyl; or
- (ii) aryl or heterocyclyl, each of which are optionally substituted with from 1 to 3 substituents independently selected from the group consisting of halogen, $C_1$-$C_6$ alkyl, $C_1$-$C_6$ alkoxy, $CF_3$, $OCF_3$;

$R_{13}$ is selected from the group consisting of H, $C_1$-$C_6$ alkyl, and $(CH_2)_n$—$C_3$-$C_8$ cycloalkyl;

$R_{14}$ is selected from the group consisting of H, $C_1$-$C_6$alkyl and CO($C_1$-$C_6$alkyl);

alternatively, $R_{13}$ and $R_{14}$, taken together with the nitrogen to which they are bonded, form a 5-6 membered heterocyclyl;

p is 1; each instance of n is independently selected from 0 and an integer from 1 to 3; and each m is independently an integer from 1 to 3.

2. The compound according to claim 1, wherein
Z is S or $SO_2$;
Y is $CH_2$; and
$R_2$ and $R_3$ are each independently H or $CH_3$.

3. The compound according to claim 2, wherein
$R_1$ is (i) $C_1$-$C_6$ alkyl; (ii) aryl optionally substituted with from 1 to 3 substituents independently selected from group consisting of halogen, $C_1$-$C_6$ alkyl, $CF_3$, $OCF_3$, $OR_{10}$, $COR_{10}$, and $COOR_{10}$; (iii) $C_3$-$C_8$ cycloalkyl; or (iv) 4- to 10-membered heterocyclyl, optionally substituted with from 1 to 3 substituents independently selected from the group consisting of halogen, $C_1$-$C_6$ alkyl, $C_1$-$C_6$ alkoxy, $CF_3$, and $OCF_3$;
$R_4$ is (i) $CONR_5R_6$; and $R_5$ and $R_6$ are defined by one of the following:
- (i) $R_5$ and $R_6$ are each independently selected from the group consisting of H, $C_1$-$C_6$ alkyl, $C_1$-$C_6$ alkoxyalkyl, $C_3$-$C_{10}$ cycloalkyl, and (3- to 8-membered heterocyclyl); or
- (ii) $R_5$ is H or $C_1$-$C_6$ alkyl, and $R_6$ is $CHR_8R_9$ or —NH-$COR_{12}$; or
- (iii) $R_5$ and $R_6$, taken together with the nitrogen atom to which they are bonded, form a 4- to 10-membered heterocyclyl optionally substituted with from 1 to 3 substituents independently selected from the group consisting of halogen, $CF_3$, $OCF_3$, $OR_{10}$, $COOR_{10}$, $NR_{10}R_{11}$, $COR_{10}$, and $CONR_{10}R_{11}$.

4. The compound according to claim 3, wherein A is CO or $SO_2$.

5. The compound according to claim 1, wherein
$R_5$ and $R_6$ are defined by one of the following:
- (i) $R_5$ and $R_6$ are each independently selected from the group consisting of H, $C_1$-$C_6$ alkyl, $C_1$-$C_6$ alkoxyalkyl, $C_3$-$C_{10}$ cycloalkyl, and (3- to 8-membered heterocyclyl); or
- (ii) $R_5$ is H or $C_1$-$C_6$ alkyl, and $R_6$ is $CHR_8R_9$ or —NH-$COR_{12}$; or
- (iii) $R_5$ and $R_6$, taken together with the nitrogen atom to which they are bonded, form a 4- to 10-membered heterocyclyl optionally substituted with from 1 to 3 substituents independently selected from the group consisting of halogen, $CF_3$, $OCF_3$, $OR_{10}$, $COOR_{10}$, $NR_{10}R_{11}$, $COR_{10}$, and $CONR_{10}R_{11}$.

6. The compound according to claim 5, wherein
$R_1$ is (i) $C_1$-$C_6$ alkyl; (ii) aryl optionally substituted with from 1 to 3 substituents independently selected from group consisting of halogen, $C_1$-$C_6$ alkyl, $CF_3$, $OCF_3$, $OR_{10}$, $COR_{10}$, and $COOR_{10}$; (iii) $C_3$-$C_8$ cycloalkyl; or (iv) 4- to 10-membered heterocyclyl, optionally substituted with from 1 to 3 substituents independently selected from the group consisting of halogen, $C_1$-$C_6$ alkyl, $C_1$-$C_6$ alkoxy, $CF_3$, and $OCF_3$; and
$R_4$ is $CONR_5R_6$.

7. A compound according to claim 1, chosen from the group consisting of
4-(4-chlorobenzoyl)-N-isobutyl-3,4-dihydro-2H-benzo[b][1,4]thiazine-6-carboxamide;
4-benzoyl-N-isobutyl-3,4-dihydro-2H-benzo[b][1,4]thiazine-6-carboxamide;
4-(4-fluorobenzoyl)-N-isobutyl-3,4-dihydro-2H-benzo[b][1,4]thiazine-6-carboxamide;
N-isobutyl-4-(4-methyl benzoyl)-3,4-dihydro-2H-benzo[b][1,4]thiazine-6-carboxamide;
N-isobutyl-4-(4-meth-oxybenzoyl)-3,4-di-hydro-2H-benzo[b][1,4]thiazine-6-carboxamide;
N-tert-butyl-4-(4-fluoro benzoyl)-3,4-dihydro-2H-benzo[b][1,4]thiazine-6-carboxamide;
N-tert-butyl-4-(4-methoxybenzoyl)-3,4-dihydro-2H-benzo[b][1,4]thiazine-6-carboxamide;
N-tert-butyl-4-(4-methylbenzoyl)-3,4-dihydro-2H-benzo[b][1,4]thiazine-6-carboxamide;
4-benzoyl-N-tert-butyl-3,4-dihydro-2H-benzo[b][1,4]thiazine-6-carboxamide;
N-tert-butyl-4-(4-chlorobenzoyl)-3,4-dihydro-2H-benzo[b][1,4]thiazine-6-carboxamide;
N-cyclopentyl-4-(4-methoxybenzoyl)-3,4-dihydro-2H-benzo[b][1,4]thiazine-6-carboxamide;
N-cyclopentyl-4-(4-fluorobenzoyl)-3,4-dihydro-2H-benzo[b][1,4]thiazine-6-carboxamide;
N-cyclopentyl-4-(4-methylbenzoyl)-3,4-dihydro-2H-benzo[b][1,4]thiazine-6-carboxamide;

4-benzoyl-N-cyclopentyl-3,4-dihydro-2H-benzo[b][1,4]
  thiazine-6-carboxamide;
N-cyclopentyl-4-(4-chlorobenzoyl)-3,4-dihydro-2H-
  benzo[b][1,4]thiazine-6-carboxamide;
4-benzoyl-N-(3-methoxypropyl)-3,4-dihydro-2H-benzo
  [b][1,4]thiazine-6-carboxamide;
4-(4-fluorobenzoyl)-N-(3-methoxypropyl)-3,4-dihydro-
  2H-benzo[b][1,4]thiazine-6-carboxamide;
N-(3-methoxypropyl)-4-(4-methylbenzoyl)-3,4-dihydro-
  2H-benzo[b][1,4]thiazine-6-carboxamide;
4-(4-chlorobenzoyl)-N-(3-methoxypropyl)-3,4-dihydro-
  2H-benzo[b][1,4]thiazine-6-carboxamide;
4-(4-methoxybenzoyl)-N-(3-methoxypropyl)-3,4-dihy-
  dro-2H-benzo[b][1,4]thiazine-6-carboxamide;
4-benzoyl-N-(1-adamantyl)-3,4-dihydro-2H-benzo[b][1,
  4]thiazine-6-carboxamide;
4-(4-fluorobenzoyl)-N-(1-adamantyl)-3,4-dihydro-2H-
  benzo[b][1,4]thiazine-6-carboxamide;
N-(1-adamantyl)-4-(4-methylbenzoyl)-3,4-dihydro-2H-
  benzo[b][1,4]thiazine-6-carboxamide;
N-(1-adamantyl)-4-(4-chlorobenzoyl)-3,4-dihydro-2H-
  benzo[b][1,4]thiazine-6-carboxamide;
N-(1-adamantyl)-4-(4-methoxybenzoyl)-3,4-dihydro-2H-
  benzo[b][1,4]thiazine-6-carboxamide;
4-benzoyl-N-isopropyl-3,4-dihydro-2H-benzo[b][1,4]thi-
  azine-6-carboxamide;
4-(4-fluorobenzoyl)-N-isopropyl-3,4-dihydro-2H-benzo
  [b][1,4]thiazine-6-carboxamide;
N-isopropyl-4-(4-methylbenzoyl)-3,4-dihydro-2H-benzo
  [b][1,4]thiazine-6-carboxamide;
4-(4-chlorobenzoyl)-N-isopropyl-3,4-dihydro-2H-benzo
  [b][1,4]thiazine-6-carboxamide;
N-isopropyl-4-(4-methoxybenzoyl)-3,4-dihydro-2H-
  benzo[b][1,4]thiazine-6-carboxamide;
4-isobutyryl-N-isopropyl-3,4-dihydro-2H-benzo[b][1,4]
  thiazine-6-carboxamide;
4-acetyl-N-tert-butyl-3,4-dihydro-2H-benzo[b][1,4]thiaz-
  ine-6-carboxamide;
N-tert-butyl-4-propionyl-3,4-dihydro-2H-benzo[b][1,4]
  thiazine-6-carboxamide;
N-tert-butyl-4-isobutyryl-3,4-dihydro-2H-benzo[b][1,4]
  thiazine-6-carboxamide;
4-acetyl-N-cyclopentyl-3,4-dihydro-2H-benzo[b][1,4]
  thiazine-6-carboxamide;
N-cyclopentyl-4-propionyl-3,4-dihydro-2H-benzo[b][1,
  4]thiazine-6-carboxamide;
N-cyclopentyl-4-isobutyryl-3,4-dihydro-2H-benzo[b][1,
  4]thiazine-6-carboxamide;
4-isobutyryl-N-(3-methoxypropyl)-3,4-dihydro-2H-
  benzo[b][1,4]thiazine-6-carboxamide;
N-(1-adamantyl)-4-propionyl-3,4-dihydro-2H-benzo[b]
  [1,4]thiazine-6-carboxamide;
N-(1-adamantyl)-4-isobutyryl-3,4-dihydro-2H-benzo[b]
  [1,4]thiazine-6-carboxamide;
N-isobutyl-4-(phenylsulfonyl)-3,4-dihydro-2H-benzo-[b]
  [1,4]thiazine-6-carboxamide;
(4-(4-fluorophenylsulfonyl)-3,4-dihydro-2H-benzo[b][1,
  4]thiazin-6-yl)(morpholino)methanone;
4-(4-fluorophenyl sulfonyl)-N-isobutyl-3,4-dihydro-2H-
  benzo[b][1,4]thiazine-6-carboxamide;
N-cyclopentyl-4-(phenylsulfonyl)-3,4-dihydro-2H-benzo
  [b][1,4]thiazine-6-carboxamide;
N-cyclopentyl-4-(4-fluorophenylsulfonyl)-3,4-dihydro-
  2H-benzo[b][1,4]thiazine-6-carboxamide;
N-tert-butyl-4-(phenylsulfonyl)-3,4-dihydro-2H-benzo
  [b][1,4]thiazine-6-carboxamide;
N-tert-butyl-4-(4-fluorophenylsulfonyl)-3,4-dihydro-2H-
  benzo[b][1,4]thiazine-6-carboxamide;
N-(3-methoxypropyl)-4-(phenylsulfonyl)-3,4-dihydro-
  2H-benzo[b][1,4]thiazine-6-carboxamide;
4-(4-fluorophenylsulfonyl)-N-(3-methoxypropyl)-3,4-di-
  hydro-2H-benzo[b][1,4]thiazine-6-carboxamide;
N-(1-adamantyl)-4-(phenylsulfonyl)-3,4-dihydro-2H-
  benzo[b][1,4]thiazine-6-carboxamide;
N-(1-adamantyl)-4-(4-fluorophenylsulfonyl)-3,4-dihy-
  dro-2H-benzo[b][1,4]thiazine-6-carboxamide;
N-isopropyl-4-(phenylsulfonyl)-3,4-dihydro-2H-benzo
  [b][1,4]thiazine-6-carboxamide;
N-tert-butyl-4-(methylsulfonyl)-3,4-dihydro-2H-benzo
  [b][1,4]thiazine-6-carboxamide;
N-isobutyl-4-(methylsulfonyl)-3,4-dihydro-2H-benzo[b]
  [1,4]thiazine-6-carboxamide;
N-cyclopentyl-4-(methylsulfonyl)-3,4-dihydro-2H-benzo
  [b][1,4]thiazine-6-carboxamide;
N-(3-methoxypropyl)-4-(methylsulfonyl)-3,4-dihydro-
  2H-benzo[b][1,4]thiazine-6-carboxamide;
N-isopropyl-4-(methylsulfonyl)-3,4-dihydro-2H-benzo
  [b][1,4]thiazine-6-carboxamide;
N,N-dimethyl-4-(phenylsulfonyl)-3,4-dihydro-2H-benzo
  [b][1,4]thiazine-6-carboxamide;
N,N-diethyl-4-(phenylsulfonyl)-3,4-dihydro-2H-benzo
  [b][1,4]thiazine-6-carboxamide;
(4-(phenylsulfonyl)-3,4-dihydro-2H-benzo[b][1,4]thi-
  azin-6-yl)(pyrrolidin-1-yl)methanone;
(4-(phenylsulfonyl)-3,4-dihydro-2H-benzo[b][1,4]thi-
  azin-6-yl)(piperidin-1-yl)methanone;
morpholino(4-(phenylsulfonyl)-3,4-dihydro-2H-benzo[b]
  [1,4]thiazin-6-yl)methanone;
4-(4-fluorophenylsulfonyl)-N,N-dimethyl-3,4-dihydro-
  2H-benzo[b][1,4]thiazine-6-carboxamide;
N,N-diethyl-4-(4-fluorophenylsulfonyl)-3,4-dihydro-2H-
  benzo[b][1,4]thiazine-6-carboxamide;
(4-(4-fluorophenylsulfonyl)-3,4-dihydro-2H-benzo[b][1,
  4]thiazin-6-yl)(pyrrolidin-1-yl)methanone;
N,N-dimethyl-4-(4-(trifluoromethyl)phenylsulfonyl)-3,4-
  dihydro-2H-benzo[b][1,4]thiazine-6-carboxamide;
N,N-diethyl-4-(4-(trifluoromethyl)phenylsulfonyl)-3,4-
  dihydro-2H-benzo[b][1,4]thiazine-6-carboxamide;
pyrrolidin-1-yl(4-(4-(trifluoromethyl)phenylsulfonyl)-3,
  4-dihydro-2H-benzo[b][1,4]thiazin-6-yl)methanone;
piperidin-1-yl(4-(4-(trifluoromethyl)phenylsulfonyl)-3,4-
  dihydro-2H-benzo[b][1,4]thiazin-6-yl)methanone;
morpholino(4-(4-(trifluoromethyl)phenylsulfonyl)-3,4-
  dihydro-2H-benzo[b][1,4]thiazin-6-yl)methanone;
(4-(4-fluorophenylsulfonyl)-3,4-dihydro-2H-benzo[b][1,
  4]thiazin-6-yl)(piperidin-1-yl)methanone;
N'-benzoyl-4-(4-fluorophenylsulfonyl)-3,4-dihydro-2H-
  benzo[b][1,4]thiazine-6-carbohydrazide;
N'-benzoyl-4-(4-(trifluoromethyl)phenylsulfonyl)-3,4-di-
  hydro-2H-benzo[b][1,4]thiazine-6-carbohydrazide;
3-(3-(trifluoromethyl)phenyl)-5-(4-(4-(trifluoromethyl)
  phenylsulfonyl)-3,4-dihydro-2H-benzo[b][1,4]thiazin-
  6-yl)-1,2,4-oxadiazole;
3-(pyridin-2-yl)-5-(4-(4-(trifluoromethyl)phenylsulfo-
  nyl)-3,4-dihydro-2H-benzo[b][1,4]thiazin-6-yl)-1,2,4-
  oxadiazole;
3-tert-butyl-5-(4-(4-(trifluoromethyl)phenylsulfonyl)-3,
  4-dihydro-2H-benzo[b][1,4]thiazin-6-yl)-1,2,4-oxadia-
  zole;
5-(4-(4-fluorophenylsulfonyl)-3,4-dihydro-2H-benzo[b]
  [1,4]thiazin-6-yl)-3-(pyridin-2-yl)-1,2,4-oxadiazole;
3-tert-butyl-5-(4-(phenylsulfonyl)-3,4-dihydro-2H-benzo
  [b][1,4]thiazin-6-yl)-1,2,4-oxadiazole;

3-tert-butyl-5-(4-(4-fluorophenylsulfonyl)-3,4-dihydro-2H-benzo[b][1,4]thiazin-6-yl)-1,2,4-oxadiazole;
3-ethyl-5-(4-(phenylsulfonyl)-3,4-dihydro-2H-benzo[b][1,4]thiazin-6-yl)-1,2,4-oxadiazole;
5-(4-(phenylsulfonyl)-3,4-dihydro-2H-benzo[b][1,4]thiazin-6-yl)-3-(pyridin-2-yl)-1,2,4-oxadiazole;
5-(4-(4-fluorophenylsulfonyl)-3,4-dihydro-2H-benzo[b][1,4]thiazin-6-yl)-3-(3-(trifluoro methyl)phenyl)-1,2,4-oxadiazole;
3-ethyl-5-(4-(4-(trifluoromethyl)phenylsulfonyl)-3,4-dihydro-2H-benzo[b][1,4]thiazin-6-yl)-1,2,4-oxadiazole;
3-ethyl-5-(4-(4-fluorophenylsulfonyl)-3,4-dihydro-2H-benzo[b][1,4]thiazin-6-yl)-1,2,4-oxadiazole;
2-(4-(4-fluorophenylsulfonyl)-3,4-dihydro-2H-benzo[b][1,4]thiazin-6-yl)-5-phenyl-1,3,4-oxadiazole;
2-phenyl-5-(4-(4-(trifluoromethyl)phenylsulfonyl)-3,4-dihydro-2H-benzo[b][1,4]-thiazin-6-yl)-1,3,4-oxadiazole;
2-methyl-5-(4-(1-methyl-1H-imidazol-4-ylsulfonyl)-3,4-dihydro-2H-benzo[b][1,4]-thiazin-6-yl)-1,3,4-oxadiazole;
6-(5-phenyl-1H-imidazol-2-yl)-4-(4-(trifluoromethyl)phenylsulfonyl)-3,4-dihydro-2H-benzo[b][1,4]thiazine;
4-(4-fluorophenylsulfonyl)-6-(5-phenyl-1H-imidazol-2-yl)-3,4-dihydro-2H-benzo[b][1,4]thiazine;
2-(4-(4-(trifluoromethyl)phenylsulfonyl)-3,4-dihydro-2H-benzo[b][1,4]thiazin-6-yl)benzo[d]oxazole; and
4-benzoyl-N-isopropyl-3,4-dihydro-1,1-dioxo-2H-benzo[b][1,4]thiazine-6-carboxamide.

8. A pharmaceutical composition comprising a compound or stereoisomer, racemate, salt thereof according to claim 1, and a pharmaceutically acceptable carrier or excipient.

9. A method of treating inflammatory pain in a mammal, the method comprising administering to a mammal in need thereof an effective amount of a compound or stereoisomer, racemate or salt or hydrate thereof according to claim 1.

10. The compound according to claim 1, wherein
A is CO or $SO_2$;
Z is S or $SO_2$; p is 1 and
$R_2$ and $R_3$ are each independently H or $CH_3$.

11. The compound according to claim 10, wherein Z is S.

12. The compound according to claim 11, wherein $R_2$ and $R_3$ are both H.

* * * * *